US006060484A

United States Patent [19]
Fritz et al.

[11] Patent Number: 6,060,484
[45] Date of Patent: May 9, 2000

[54] ANTI-VIRAL METHOD

[75] Inventors: James E. Fritz, McCordsville; Stephen W. Kaldor, Indianapolis; Jeffrey A. Kyle, Fishers; John E. Munroe, Indianapolis, all of Ind.

[73] Assignee: Eli Lilly and Company, Indianapolis, Ind.

[21] Appl. No.: 09/214,533

[22] PCT Filed: May 2, 1997

[86] PCT No.: PCT/US97/07431

§ 371 Date: Jan. 6, 1999

§ 102(e) Date: Jan. 6, 1999

[87] PCT Pub. No.: WO97/41846

PCT Pub. Date: Nov. 13, 1997

Related U.S. Application Data

[60] Provisional application No. 60/016,870, May 6, 1996.

[51] Int. Cl.$^7$ .................... A61K 31/47; A61K 31/445; A61K 31/27; A61K 31/17; A61K 31/165

[52] U.S. Cl. .................... 514/311; 514/365; 514/357; 514/438; 514/471; 514/485; 514/488; 514/546; 514/596; 514/617; 514/634

[58] Field of Search .................... 514/617, 596, 514/488, 546, 634, 357, 311, 485, 438, 471, 365

[56] References Cited

U.S. PATENT DOCUMENTS

| | | | |
|---|---|---|---|
| 2,703,809 | 3/1955 | Ritchie | 260/469 |
| 2,744,100 | 5/1956 | Subluskey | 260/97 |
| 2,744,102 | 5/1956 | Suibluskey | 260/99 |
| 2,750,382 | 12/1956 | Bible et al. | 260/247.2 |
| 2,750,405 | 6/1956 | Ritchie et al. | 514/510 |
| 2,750,407 | 6/1956 | Ritchie | 260/473 |
| 2,753,357 | 7/1956 | Bible et al. | 260/343.3 |
| 2,759,014 | 8/1956 | Bible | 260/473 |
| 2,767,162 | 10/1956 | Picha | 260/103 |
| 2,854,474 | 9/1958 | Bible | 260/468.5 |
| 2,862,955 | 10/1958 | Hoehn | 260/468.5 |
| 2,947,778 | 8/1960 | Bible | 260/468.5 |
| 3,014,957 | 12/1961 | Hoehn | 260/465 |
| 3,038,930 | 6/1962 | Bible | 260/488 |
| 3,668,223 | 6/1972 | Jones | 424/279 |
| 4,252,804 | 2/1981 | Jouille et al. | 544/91 |
| 4,333,941 | 6/1982 | Baratz et al. | 424/267 |
| 5,015,644 | 5/1991 | Roth et al. | 514/247 |
| 5,276,053 | 1/1994 | Johnson | 514/437 |
| 5,321,044 | 6/1994 | Peters et al. | 514/437 |

FOREIGN PATENT DOCUMENTS

| | | |
|---|---|---|
| 0 540 143 A2 | 8/1992 | European Pat. Off. . |
| 0 806 203 A2 | 5/1997 | European Pat. Off. . |
| WO 97 41822 | 11/1997 | WIPO . |
| WO 97 41860 | 11/1997 | WIPO . |
| WO 97 41861 | 11/1997 | WIPO . |
| WO 97 42145 | 11/1997 | WIPO . |
| WO 97 42155 | 11/1997 | WIPO . |
| WO 97 42156 | 11/1997 | WIPO . |

OTHER PUBLICATIONS

Ueda, et al.: "The Leaf Oil and Resin Acid Compopnents of Lacebark Pine, *Pinus bungeana* Zucc," Tottori Diagaku Kogakubu Kenkyu Hokiku, vol. 20, No. 1, 1989 Japan, pp. 87–96.

CAPLUS Abstr., No. 74:112247, Turner, et al., J. Chem. Soc. C., 1971, vol. 3, 547–553.

CAPLUS Abstr., No. 81:169653, Cambie, et al., Aust. J. Chem., 1974, vol. 27, No. 9, 2001–2016.

CAPLUS Abstr., No. 85:177668, Tahara, et al., chem. Pharm. Bull., 1976, vol. 24, No. 7, 1497–1501.

CAPLUS Abstr., No. 121:116357, Standley, et al., J. Atmos. Chem., 1994, vol. 18, No. 1, 1–15.

CAPLUS Abstr., No. 124:317517, Matsumoto, et al., chem. Pharm. Bull., 1996, vol. 44, No. 3, 530–533.

CAPLUS Abstr., No. 99:212742, Burnell, et al., Can. J. Chem., 1983, vol. 61, No. 11, 2461–2465.

CAPLUS Abstr., No. 102:79171, Burnell, et al., Synth. Commun., 1984, vol. 14, No. 13, 1229–1237.

CAPLUS Abstr., No. 113:152784, Cambie, et al., Aust. J. Chem., 1990, vol. 43, No. 5, 883–893.

CAPLUS Abstr., No. 121:35902, Matsumoto, et al., Chem. Pharm. Bull., 1993, vol. 41, No. 11, 1960–1964.

Chemical Abstracts, Abstract #2502; vol. 50, No. 4, Feb. 25, 1956, Michitoshi Ohta.

G. Defaye–Duchateau, "Oxydations dans la serie de l'acide dehydroabietique," 1964, Paris, 1469–1473.

Georges Dupont, et al., "Oxydation de l'acide abietique parl'acetate mercurique.Derives de l'acide dehydroabietique substitutes dans le cycle B," 1955, Paris, 708–715.

J. C. Sircar, et al., "free–Radical Bromoination of Methyl Abietate by N–Bromosuccinimide and Solvolysis of the Products,", vol. 35, No. Sep. 9, 1970, 3090–3093.

Chem. Abstr. vol. 112, No. 21, May 21, 1990, Abstract No. 198830, Sugai, et al.

Chem. Abstr., vol. 110, No. 9, Feb. 27, 1989, Abstract No. 75825, Nishi, et al.

Chem. Abstr., vol. 91, No. 23, Dec. 3, 1979, Abstract No. 193454, Pelletier, et al.

Chem. Abstr., vol. 81, No. 7, Aug. 19, 1974, Abstract No. 25842, Wirthlin, et al.

Chem. Abstr., vol. 121, No. 17, Oct. 24, 1994, Abstract No. 195010, Tagat, et al.

Chem. Abstr., vol. 120, No. 11, Mar. 14, 1994, Abstract No. 134850, Selwod, et al.

Chem. Abstr., vol. 61, No. 5, Aug. 31, 1964, Abstract No. 5699f, Tahara, et al.

(List continued on next page.)

*Primary Examiner*—Bernard Dentz
*Attorney, Agent, or Firm*—Arlene K. Musser; Janet T. McClain

[57] ABSTRACT

The present invention provides compounds which inhibit an envelope virus by inhibiting the fusion of the virus with the host cell. The virus may be inhibited in an infected cell, a cell susceptible of infection or a mammal in need thereof.

5 Claims, No Drawings

OTHER PUBLICATIONS

Helvetica Chemica Acta., vol. 57, No. 2, Mar. 13, 1974, Basel Ch., 351–368.

Tetrahedron, vol. 21, No. 8, Aug. 1965, Oxford GB, 2133–2154.

Database Crossfire, Beilstein Informationssysteme, GMBH. Frankfurt DE, Beilstein registry No. 5483432, XP002031126, Cruz Frederico G., et al., Phytochemistry, vol. 31, No. 8, 1992, pp. 2793–2796.

Chem. Abstr., vol. 110, No. 21, Nov. 20, 1989, Abstract No., 195166, Node, et al.

Chem. Abstr., vol. 88, No. 25, Jun. 19, 1978, Abstract No. 191065, Ichinohe.

Chem. Abstr., vol. 83, No. 11, Sep. 15, 1975, Abstract No. 97643, Ichinohe.

Chem Abstr., vol. 81, No. 5, Aug. 5, 1974, Abstract No. 25842, Wirthlin, et al.

Database Crossfire, Beilstein Informationssysteme, GMBH. Frankfort DE, Beilstein registry No. 4824891, XP002060909, Richard C. Cambie, et al., Australian Journal of Chemistry, vol. 44, No. 11, 1991, pp. 1553–1573.

Database Crossfire, Beilstein Informationssysteme, GMBH. Frankfurt DE, Beilstein registry No. 2179057, XP002060813, Richard C. Cambie, et al., Australian Journal of Chemistry, vol. 27, 1974, pp. 2413–2419.

Database Crossfire, Beilstein Informtionssysteme, GMBH. Frankfurt DE, Beilstein registry No. 2887142, XP002060814, Richard C. Cambie, et al., Australian Journal of Chemistry, vol. 25, 1972, pp. 974–980.

Database Crossfire, Beilstein Informatiossysteme, GMBH. Frankfurt DE, Beilstein registry No. 2920097, XP002060815, Richard C. Cambie, et al., Australian Journal of Chemistry, vol. 27, 1974, pp. 2001–2011.

Compets Rendus De l'academie Bulgare des sciences, vol. 48, No. 11–12, 1995.

ANTI-VIRAL METHOD

This application is a 371 of PCT/US97/07431 May 2, 1997, which claims priority from U.S. Provisional Application No. 60/016,870 filed May 6, 1996.

Influenza viruses cause an infectious disease for which there is no adequate therapeutic agent. The disadvantages of existing treatments include the onset of clinical resistance within thirty six hours and the ineffectiveness of the agents against influenza B. Killed influenza virus vaccines have been available for over sixty years. However, these vaccines have not lessened the morbidity, mortality or severe financial loss caused by this disease. It follows that an agent which treats or prevents an influenza infection or is effective at preventing the clinical symptoms associated with an influenza infection will result in a significant benefit to society.

Currently, the only compounds approved for the therapeutic and prophylactic treatment of influenza infections are the adamantanes: amantadine and rimantadine. These compounds inhibit influenza A by inhibiting the function of the M2 ion channel activity of the virus. Amantadine is a potent in vitro inhibitor of influenza A virus as demonstrated by standard antiviral assays such as the plaque reduction assay. Amantadine is effective in reducing the duration of fever and other systemic complaints including but not limited to myalgia (muscular ache) and fatigue when administered to individuals infected with influenza A within forty-eight hours of the onset of clinical symptoms. It has also been observed that amantadine results in a one hundred-fold decrease of virus titer in the nasal washes of human volunteers infected with wild-type influenza virus which correlates with a dramatic decrease in fever score. Thus, in vitro influenza inhibition is predictive of useful in vivo effects, i.e. a reduction of the clinical symptoms associated with the influenza infection.

The present invention derives from the fact that influenza is an enveloped virus which dictates that the virus envelope must be fused with the endosomal membrane of the host cell in order to initiate the process of introducing its genetic information into the cell. Because this process is common to all enveloped viruses, it is an attractive target for antiviral chemotherapy. Examples of envelope viruses which are inhibited according to the present invention include influenza, bovine diarrheal, hepatitis C, tick borne encephalitis and the like. The fusion domain of the envelope glycoprotein of influenza, hemagglutinin (HA) has been well-characterized. see, White J. M., Annu. Rev. Physiol. vol. 52, pages 675–697 (1990) which is herein incorporated by reference.

Influenza virus HA provides at least two distinct functions: 1) recognition of the host cell receptor, i.e., sialic acid residues on glycoconjugates, and 2) fusion of the viral envelope with the endosomal membrane. Both functions are essential for the propagation of influenza virus in vitro and in vivo. During viral maturation, monomeric HA is inserted into a lipid bilayer, post-translationally modified and oligomerized into a trimer of identical subunits (trimeric HA). The infectivity of the progeny virus is contingent upon a site-specific cleavage of HA by host cell protease(s). This cleavage results in the formation of two polypeptide chains, HA1 and HA2, which remain associated by non-covalent interactions as well as by an intermolecular and intramolecular disulfide bonds.

It has been established that influenza HA has two functionally relevant conformations. One conformation (Form A) exists as a metastable structure at neutral pH and mediates receptor recognition. Following receptor mediated binding to the host cell, the virus is transported to the endosomal compartment where it encounters an acidic environment. The low pH triggers a dramatic structural rearrangement of HA (Form A) which results in the formation of the other, more stable conformation of HA (Form B).

Form B of HA is required for fusion of the virus envelope with the endosomal membrane. It -continued

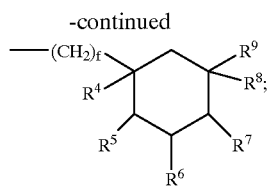

where:

R$^1$ is hydrogen, C$_1$-C$_4$ alkyl, benzyl or pyridyl(C$_1$-C$_4$ alkyl), thienyl(C$_1$-C$_4$ alkyl) or furyl(C$_1$-C$_4$ alkyl);

each b, d and f are independently 1, 2 or 3;

c is 0, 1 or 2;

R$^2$ and R$^3$ are independently hydrogen, phenyl, pyridyl, thiazolyl, quinolyl, tetrahydroquinolyl, cyclohexyl, cyclohexenyl or phenyl or pyridyl substituted with halo, C$_1$-C$_4$ alkyl or C$_1$-C$_4$ alkoxy;

R$^4$ is hydrogen, C$_1$-C$_4$ alkyl or phenyl;

R$^5$ is hydrogen or R$^5$ and R$^6$ combine to form a bond;

R$^6$ and R$^7$ are independently hydroxy, —OC(O)CH$_3$, =O, —OC(O)NHR$^{6a}$, —O—(R$^{6b}$)$_x$— or R$^6$ and R$^7$ combine to form a bond;

R$^{6a}$ is hydrogen, C$_1$-C$_4$ alkyl, phenyl or benzyl;

R$^{6b}$ is an amino acid;

x is 1, 2 or 3;

R$^8$ and R$^9$ are independently hydrogen or C$_1$-C$_4$ alkyl; with the proviso that when R$^5$ and R$^6$ combine to form a bond, R$^7$ must be hydrogen, and when R$^6$ and R$^7$ combine to form a bond, R$^5$ must be hydrogen;

or a pharmaceutically acceptable salt thereof.

The present invention also relates to a compound of formula IA:

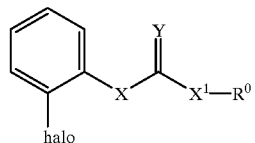

IA wherein:

X is a bond, —NH—, —CH$_2$—, —O— or —S—;

Y is oxygen, sulfur or nitrogen;

X$^1$ is —O—, —N(R$^1$)— or —CH$_2$—;

R$^0$ is a group of the formula:

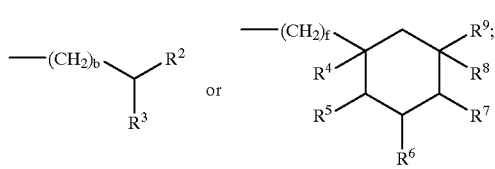

where:

R$^1$ is hydrogen, C$_1$-C$_4$ alkyl, benzyl or pyridyl (C$_1$-C$_4$ alkyl), thienyl (C$_1$-C$_4$ alkyl) or furyl (C$_1$-C$_4$ alkyl);

b and f are independently 1, 2 or 3;

R$^2$ and R$^3$ are independently hydrogen, phenyl, pyridyl, thiazolyl, quinolyl, tetrahydroquinolyl, cyclohexyl, cyclohexenyl or phenyl or pyridyl substituted with halo, C$_1$-C$_4$ alkyl or C$_1$-C$_4$ alkoxy;

R$^4$ is hydrogen, C$_1$-C$_4$ alkyl or phenyl;

R$^5$ is hydrogen or R$^5$ and R$^6$ combine to form a bond;

R$^6$ and R$^7$ are independently hydroxy, —OC(O)CH$_3$, =O, —OC(O)NHR$^{6a}$, —O—(R$^{6b}$)$_x$— or R$^6$ and R$^7$ combine to form a bond;

R$^{6a}$ is hydrogen, C$_1$-C$_4$ alkyl, phenyl or benzyl;

R$^{6b}$ is an amino acid;

x is 1, 2 or 3;

R$^8$ and R$^9$ are independently hydrogen or C$_1$-C$_4$ alkyl; with the proviso that when R$^5$ and R$^6$ combine to form a bond, R$^7$ must be hydrogen, and when R$^6$ and R$^7$ combine to form a bond, R$^5$ must be hydrogen;

or a pharmaceutically acceptable salt thereof.

In addition, the present invention relates to a compound of formula IB:

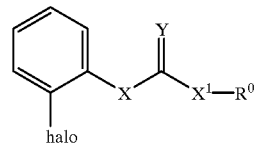

IB a is 1, 2 or 3;

X is a bond, —NH—, —CH$_2$—, —O— or —S—;

Y is oxygen, sulfur or nitrogen;

R is halo or C$_1$-C$_4$ alkyl or C$_1$-C$_4$ alkoxy;

X$^1$ is —O—, —N(R$^1$)— or —CH$_2$—;

R$^0$ is a group of the formula:

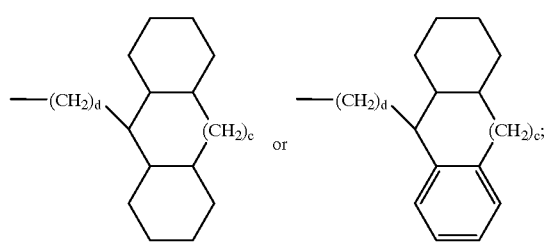

where:

R$^1$ is hydrogen, C$_1$-C$_4$ alkyl, benzyl or pyridyl (C$_1$-C$_4$ alkyl), thienyl (C$_1$-C$_4$ alkyl) or furyl (C$_1$-C$_4$ alkyl);

each d is independently 1, 2 or 3;

c is 0, 1 or 2;

or a pharmaceutically acceptable salt thereof.

The present invention further provides pharmaceutical formulations comprising a compound of the present invention, or a pharmaceutically acceptable salt thereof, in combination with a pharmaceutically acceptable carrier, diluent or excipient therefor.

All temperatures stated herein are in degrees Celsius (° C.). All units of measurement employed herein are in weight units except for liquids which are in volume units.

"Halo" represents chloro, fluoro, bromo or iodo.

As used herein, the term "C$_1$-C$_4$ alkyl" represents a straight or branched alkyl chain having from one to four carbon atoms. Typical C$_1$-C$_4$ alkyl groups include methyl, ethyl, propyl, isopropyl, butyl, isobutyl, sec-butyl, t-butyl and the like.

The term "C$_1$-C$_4$ alkylthio" represents a straight or branched alkyl chain having from one to four carbon atoms attached to an oxygen atom. Typical C$_1$-C$_4$ alkoxy groups include methoxy, ethoxy, propoxy, isopropoxy, butyloxy and the like.

All amino acid abbreviations used in this disclosure are those accepted by the United States Patent and Trademark Office as set forth in 37 C.F.R. §1.822(b)(1994).

The compounds of the present invention have from 0 to 3 asymmetric centers. As a consequence of these asymmetric centers, the compounds of the present invention occur as racemates, racemic mixtures and as individual enantiomers. All asymmetric forms, individual isomers and combinations thereof, are within the scope of the present invention.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds used in the claimed method are those compounds of formula I where:

a is 1 or 2;
Y is oxygen or sulfur;
R is halo, methyl or ethyl;
$R^1$ is hydrogen or methyl;
b, d and f are each 1;
c is 0 or 2;

$R^2$ and $R^3$ are independently phenyl, pyridyl, quinolyl, tetrahydroquinolyl or cyclohexyl;
or a pharmaceutically acceptable salt thereof.

Of these compounds, more preferred are those compounds of formula I where:
X is —NH— or —CH$_2$—;
$R^0$ is a group of the formula:

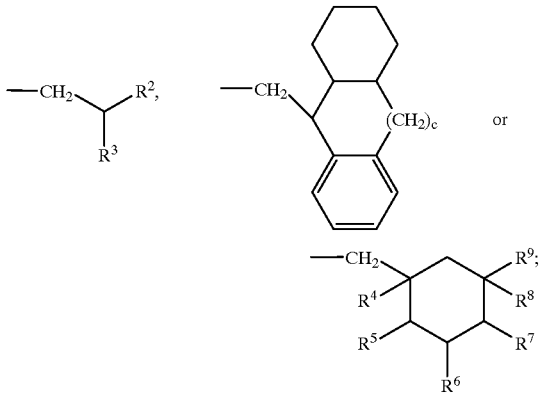

$R^4$ is hydrogen, methyl or phenyl;
$R^5$ is hydrogen or $R^5$ and $R^6$ combine to form a bond;
$R^6$ and $R^7$ are independently hydroxy, —OC(O)CH$_3$, =O, or $R^6$ and $R^7$ combine to form a bond;
$R^8$ and $R^9$ are independently hydrogen or methyl;
with the proviso that when $R^5$ and $R^6$ combine to form a bond, $R^7$ must be hydrogen, and when $R^6$ and $R^7$ combine to form a bond, $R^5$ must be hydrogen;
or a pharmaceutically acceptable salt thereof.

Of these compounds, more preferred are those compounds of formula I where:
X is —NH—;
$X^1$ is —N($R^1$)—;
R is chloro or methyl;
$R^1$ is hydrogen;
or a pharmaceutically acceptable salt thereof.

The most preferred compounds are:
N-(2-chlorophenyl)-N'-[2-cyclohexyl-2-(pyrid-2-yl)-ethyl]urea;
N-(2-chlorophenyl)-N'-[2-cyclohexyl-2-(pyrid-2-yl)ethyl]urea hydrochloride;

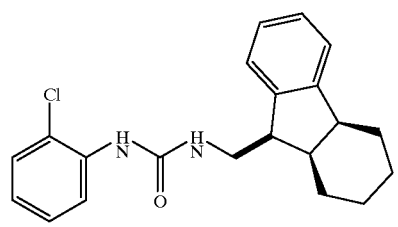

N-(2-chlorophenyl)-N'-[2-phenyl-2-(pyrid-4-yl)ethyl]urea;
or a pharmaceutically acceptable salt thereof.

The compounds of formula I may be prepared using procedures known in the art. For example, the following Reactions may be used, alone or in combination to provide the desired compounds. Once a reaction is complete, the intermediate compound may be isolated by procedures well-known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

For example, the compounds of formula I where X is —NH—, Y is oxygen and $X^1$ is —N($R^1$)— may be prepared by coupling an appropriately substituted phenyl isocyanate of the formula

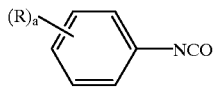

with a suitably substituted amine of the formula $H_2N$—$R^0$ in an aprotic solvent. Typical solvents suitable for use in this process include dimethylformamide or ethyl acetate. Solvent choice is not critical so long as the solvent employed is inert to the ongoing reaction and the reactants are sufficiently solubilized to effect the desired reaction. The reaction is generally substantially complete after about 1 to 36 hours when conducted at a temperature in the range of from about 10° C. to about 100° C. The reaction is preferably conducted at a temperature in the range of from about 20° C. to about 80° C. for about 1 to 12 hours.

The phenyl isocyanates and amines used above are commercially available or readily prepared according to procedures known in the art.

Specifically, the phenyl isocyanates may be prepared by reacting an appropriately substituted aniline with triphosgene and triethylamine in a suitable solvent. Typical solvents suitable for use in this process include methylene chloride or chloroform. The reaction is generally substantially complete after about 15 minutes to 3 hours when conducted at a temperature in the range of from about 0° C. to about 40° C. The reaction is preferably conducted at a temperature in the range of from about 0° C. to room temperature for up to 1 hour. The anilines are commercially available or in the case of 2-chloro-3-methyl aniline may be formed by hydrogenation of commercially available 2-chloro-3-nitrotoluene, for example by catalytic hydrogenation over 5% platinum-on-carbon.

The amines may be prepared by reacting a suitably substituted carboxylic acid (or an hydrogenated derivative of a carboxylic acid) with an oxalyl halide in a suitable solvent such as toluene or benzene to provide the corresponding acyl halide. Preferred oxalyl halides include the chloride and bromide. The reaction is generally substantially complete after about 6 to 24 hours when conducted at a temperature in the range of from about 20° C. to about 40° C. The reaction is preferably conducted at room temperature for about 16 to 20 hours. Ammonia gas is bubbled through a solution of the acyl halide in diethyl ether to provide the corresponding amide which is then reduced to provide the desired amine. The reaction is generally substantially complete after about 2 to 30 minutes when conducted at a temperature of about 0° C.).

For example, the amide may be reduced by refluxing the amide and a borane/tetrahydrofuran complex or a borane/methyl sulfide complex in tetrahydrofuran for about 1 to 24 hours. When the reaction is substantially complete, the reaction is quenched by the addition of an alcohol, for example methanol, followed by the precipitation of the complex by the addition of an acid, for example ethereal hydrogen chloride. The desired amine compound is then obtained by the addition of a base such as sodium hydroxide or sodium bicarbonate.

Alternatively, the amines may be prepared by reacting a suitably substituted alkyl halide with sodium azide in an aprotic solvent to provide the corresponding alkyl azide which is then reduced to provide the desired amine. Preferred alkyl halides are the alkyl chlorides. Typical solvents suitable for use in this process include dimethylformamide. Solvent choice is not critical so long as the solvent employed is inert to the ongoing reaction and the reactants are sufficiently solubilized to effect the desired reaction. The reaction is generally substantially complete after about 24 hours when conducted at a temperature of about 0° C. to room temperature. The alkyl azide is reduced using procedure known in the art. For example, the azide can be catalytically reduced using a catalyst such as platinum oxide or the azide can by reduced by reaction with a suitable reducing agents such as lithium aluminum hydride (LAH) or sodium borohydride.

The amines where $R^0$ contains a cyclohexyl or benzyl moiety may be prepared by reacting cyclohexyl acetonitrile or benzyl cyanide with a base in a suitable solvent such as dimethylformamide to form the corresponding α-carbanion. Typical bases include potassium t-butoxide or lithium bis (trimethylsilyl)amide. The reaction is generally substantially complete after about 2 to 24 hours when conducted at a temperature in the range of from about 15° C. to about 40° C. The reaction is preferably conducted at room temperature for about 2 to 6 hours. The carbanion is then reacted with chloropyridine or 2-chloroquinoline to provide the corresponding nitriles which are then hydrogenated using procedures known in the art to provide the desired amine. For example, the nitrile may be catalytically hydrogenated using a suitable catalyst such as 5% palladium-on-carbon, Raney nickel and the like. Typical solvents suitable for use in this process include a mixture of ethanol and hydrochloric acid. The reaction is generally substantially complete after about 12 to 36 hours when conducted at a temperature in the range of from about 10° C. to about 40° C. The reaction is preferably conducted overnight at room temperature. Cyclohexyl acetonitrile may be prepared from cyclohexyl methyl bromide using sodium cyanide in dimethylformamide The amines where $R^0$ contains a dibenzosuberyl moiety may be prepared by reacting dibenzosuberol with thionyl chloride in a suitable solvent such as methylene chloride to provide the corresponding alkyl chloride. The reaction is generally substantially complete after about 12 to 36 hours when conducted at a temperature in the range of from about 20° C. to about 40° C. The reaction is preferably conducted overnight at room temperature. This alkyl chloride is refluxed with copper (I) cyanide in toluene for 2 days to provide the corresponding nitrile which is then hydrogenated as described above to provide the desired amine.

The amines where $R^0$ contains a 5,5-dimethyl-3-phenyl-2-cyclohexanol may be prepared substantially as described in Mestres et al., Tetrahedron, volume 50, page 2571 (1994). For example, in a tandem Michael-Dieckmann decarboxylative annulation of trans-βmethylcinnamic acid and 3,3-dimethylacrylic acid, the cyclohexenone was stirred with diethylaluminum cyanide in tetrahydrofuran at room temperature overnight to provide 3-cyano-5,5-dimethyl-3-phenylcyclohexanone which was then hydrogenated over 5% rhodium on alumina to give the corresponding amine.

The N-methylated ureas are prepared by protecting a primary amine, for example with t-butoxy carbonyl. The protected amine is then alkylated by deprotonating the protected amine with a base such as sodium hydride, followed by reaction with iodomethane. The methylated, protected amine is then deprotected, for example by treatment with from about 3 to 7 equivalents, preferably about 5 equivalents of trifluoroacetic acid in a suitable solvent such as methylene chloride. The reaction is generally substantially complete after about 4 to 8 hours when conducted at a temperature in the range of from about 20° C. to about 60° C. The reaction is preferably conducted at room temperature for about 5 to 7 hours. The alkylated amine is then coupled to a phenyl isocyanate as described above to form the desired N-methylated urea.

The compounds of formula I where X is —NH— and Y is sulfur are prepared by coupling an appropriately substituted phenyl isothiocyanate to an amine substantially as described above.

The ureas and thioureas prepared above may also be used to make other ureas. For example, the acetylated derivatives of hydroxy-containing ureas are prepared by reacting the hydroxy-containing urea with acetyl chloride or acetyl bromide in the presence of a base. A preferred base is pyridine. A suitable solvent is methylene chloride. The reaction is generally substantially complete after about 2 to 6 hours when conducted at a temperature in the range of from about 10° C. to about 40° C. The reaction is preferably conducted at room temperature for about 3 to 5 hours.

The L-alanine derivatives of hydroxy-containing ureas are prepared by reacting the hydroxy-containing urea with amino-protected L-alanine in the presence of a catalyst, for example 4-dimethylaminopyridine and a coupling agent in a suitable solvent such as diethyl ether. The reaction is generally substantially complete after about 2 to 24 hours when conducted at a temperature in the range of from about 10° C. to about 40° C. The reaction is preferably conducted at room temperature for about 12 to 18 hours.

The hydroxy-containing ureas may be eliminated via a two step process to provide the corresponding alkenes. First the alcohol is treated with methanesulfonyl chloride or toluenesulfonyl chloride in a suitable solvent such as methylene chloride to form the corresponding mesylate or tosylate. The mesylate is then eliminated with 1,8-diazabicyclo[5.4.0]undec-7-ene (DBU) in a suitable solvent such as toluene to provide an alkene. The reaction is generally substantially complete after about 2 to 6 hours when conducted at a temperature of from about room temperature to about the reflux temperature of the mixture. The reaction is preferably conducted at a temperature in the range of from about 40° C. to the reflux temperature of the mixture for about 4 to 6 hours. These alkenes may be catalytically hydrogenated using procedures known in the art to provide the corresponding saturated alkyl. A preferred catalyst is platinum oxide.

The hydroxy-containing ureas may be oxidized to provide the corresponding ketones. For example, an hydroxy-containing urea may be reacted with an oxidizing agent such as pyridinium chlorochromate in a suitable solvent such as methylene chloride. The reaction is generally substantially complete after about 1 hour when conducted at room temperature. The reaction is preferable carried out under anhydrous conditions, for example in the presence of molecular sieves.

The compounds of formula I where X is —CH$_2$— and Y is oxygen are prepared by coupling an amine of formula H$_2$N—R$^0$ to an acyl chloride in the presence of a base. Typical bases include sodium bicarbonate, sodium hydroxide, potassium hydroxide, ammonium hydroxide and the like. Suitable solvents include a water/chloroform or water/methylene chloride mixture. The reaction is generally substantially complete after about ten minutes to 2 hours when conducted at a temperature in the range of from about −10° C. to about 10° C. The reaction is preferably conducted at about 0° C. for about 30 minutes to 1 hour. The acyl chlorides are commercially available or may be prepared as described above.

The compounds of formula I where X is —O— and Y is oxygen or sulfur are prepared by treating a phenol or thiophenol with triphosgene in a suitable solvent such as methylene chloride to provide the corresponding chloroformate and chlorothioformate compounds. The chloroformate or chlorothioformate compound is then coupled to an amine substantially as described above.

Alternatively, the compounds of formula I where X is —O—, Y is oxygen and X$^1$ is nitrogen are prepared by coupling an appropriately substituted phenyl isocyanate with an appropriately substituted ethanol reactant of the formula HO—R$^0$ substantially as described above.

The compounds of formula I where X is —NH— and Y is nitrogen are prepared by reacting the hydrochloride salt of an appropriately substituted aniline and a cyanamide followed by the addition of an aqueous base such as sodium bicarbonate to provide the desired guanidine compound. A suitable solvent is chlorobenzene. The reaction is generally substantially complete after about 1 to 4 hours when conducted at a temperature in the range of from about 100° C. to about 150° C. The reaction is preferably conducted at about 120° C. to about 130° C. for about 1 to 3 hours.

The following Preparations and Examples further illustrate specific aspects of the present invention. It is to be understood, however, that these examples are included for illustrative purposes only and are not intended to limit the scope of the invention in any respect and should not be so construed.

EXAMPLE 1

A. N-(2-Chlorophenyl-N'-(2,2-diphenylethyl)-urea

A solution of 2,2-diphenylethylamine (2.0 g, 10.1 mmol) in 15 ml of N,N-dimethylformamide (DMF) was cooled to 0° C. and treated with 2-chlorophenyl isocyanate (1.46 g, 12.2 mmol) under nitrogen (N$_2$). The reaction solution was stirred at room temperature for 15 minutes and partitioned between ethyl acetate (EtOAc) and water (H$_2$O). The organic layer was washed with sodium bicarbonate (NaHCO$_3$) and brine, dried over sodium sulfate (Na$_2$SO$_4$), filtered and concentrated in vacuo to provide a white solid. Yield: 3.34 g, 94%.

EXAMPLE 2

N-(2-Chlorophenyl)-O-(2,2-diphenylethyl)-urethane

The compound was prepared substantially in accordance with the procedure detailed in Example 1, using 2,2-diphenylethanol (0.56 g, 2.8 mmol) and 2-chlorophenyl isocyanate (0.34 ml, 2.8 mmol) in 25 ml of DMF. The crude material was purified using flash silica gel chromatography (eluent of 3% EtOAc in hexanes) followed by recrystallization (hexanes/EtOAc).

Yield: 0.68 g of a white solid (69%).

EXAMPLE 3

A.

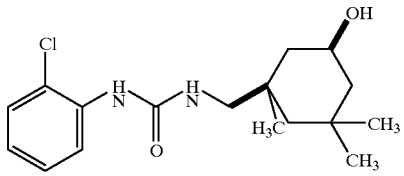

The compound was prepared substantially in accordance with the procedure detailed in Example 1, using (+,−)-3-aminomethyl-3,5,5-trimethylcyclohexanol (cis and trans, 8.50 g, 49.6 mmol) and 2-chlorophenyl isocyanate (9.0 ml, 74.4 mmol) in 745 ml of DMF. The reaction mixture was concentrated in vacuo to provide an oil which was redissolved in cold diethyl ether ($Et_2O$) resulting in the precipitation of a white solid which was isolated by filtration.

Yield: 3.36 g (20%).

B.

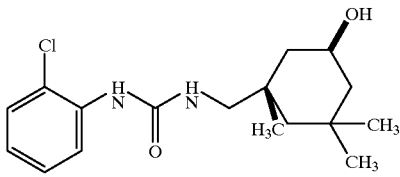

The filtrate from Example 3A was concentrated in vacuo to provide an oil which was purified using flash chromatography (eluent of 5% methanol (MeOH) in methylene chloride ($CH_2Cl_2$)) to provide a white foam (3.71 g, 23%). A small portion of the foam was recrystallized (hexanes/$CH_2Cl_2$) to provide a white solid.

EXAMPLE 4

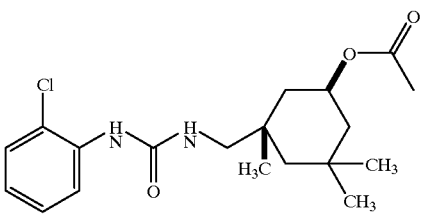

To a solution of the compound of Example 3B (0.3 g, 0.9 mmol) in 7 ml of $CH_2Cl_2$, was added acetyl chloride (0.08 ml, 1.1 mmol) and pyridine (0.2 ml, 2.8 mmol), under $N_2$. After stirring the reaction mixture at room temperature for 4 hours, the mixture was diluted with $CH_2Cl_2$, washed consecutively with 1.0N hydrochloric acid (HCl), $NaHCO_3$ and brine, dried over $Na_2SO_4$, filtered and then concentrated in vacuo. The crude material was purified using flash chromatography.

Yield: 0.15 g of a white solid (45%).

EXAMPLE 5

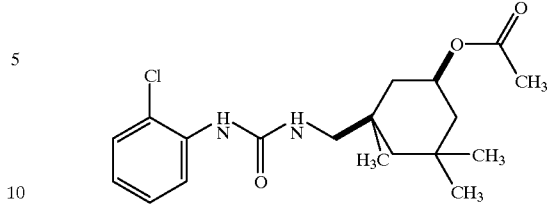

The compound was prepared substantially in accordance with the procedure detailed in Example 4, using the compound of Example 3A (0.3 g, 0.9 mmol), acetyl chloride (0.08 ml, 1.1 mmol) and pyridine (0.2 ml, 2.8 mmol) in 7 ml of $CH_2Cl_2$. The crude product was purified using flash chromatography.

Yield: 0.19 g of a white solid (57%).

EXAMPLE 6

N-(2-Chlorophenyl-N'-(2,2-diphenylethyl)-thiourea

The compound was prepared substantially in accordance with the procedure detailed in Example 1, using 2,2-diphenylethylamine (1.61 g, 8.1 mmol) and 2-chlorophenyl isothiocyanate (1.1 ml, 8.2 mmol) in 30 ml of DMF. The crude material was purified by recrystallization (hexanes/EtOAc).

Yield: 2.68 g of a white solid (90%).

EXAMPLE 7

N-(2,2-Diphenylethyl)-2-chlorophenylamide

A mixture of 2,2-diphenylethylamine (0.61 g, 3.1 mmol) in chloroform ($CHCl_3$)/$H_2O$ (1:1, 40 ml) was treated with $NaHCO_3$ (0.50 g, 6.0 mmol) and O-chlorobenzoyl chloride (0.4 ml, 3.2 mmol) at 0° C. The reaction mixture was stirred for 45 minutes and then filtered. The resultant layers of the filtrate were separated, and the organic layer was washed three times with $NaHCO_3$ and twice with 0.2N HCl, dried over $Na_2SO_4$, filtered and then concentrated in vacuo. The crude material was purified by recrystallization (hexanes/EtOAc).

Yield: 0.44 g of a white solid (44%).

EXAMPLE 8

N-(2,2-Diphenylethyl)-2-chlorobenzyl amide

A suspension of 2-chlorophenylacetic acid (5.0 g, 29.3 mmol) in toluene (25 ml) was treated with oxalyl chloride (3.6 ml, 41.0 mmol) at room temperature, under $N_2$. The reaction mixture was reacted at 50° C. for 48 hours and then cooled to room temperature and concentrated in vacuo to provide a clear oil (5.47 g, 98%). This oil (5.47 g, 28.9 mmol) was reacted with 2,2-diphenylethylamine (5.70 g, 28.9 mmol) in the presence of $NaHCO_3$ (4.85 g, 57.8 mmol) in 30 ml of a 1:1 $CHCl_3$/$H_2O$ mixture substantially in accordance with the procedure detailed in Example 7. The crude material was purified by recrystallization (hexanes/EtOAc).

Yield: 2.38 g of a white solid (23%).

EXAMPLE 9

A. 2-Chlorophenyl thioisocyanate

A mixture of 2-chlorothiophenol (0.57 ml, 5 mmol) and triphosgene (1.48 g, 5 mmol) in 50 ml of $CH_2Cl_2$ was stirred at room temperature overnight, under $N_2$. This reaction mixture was concentrated in vacuo to provide a residue which was suspended in hexanes and filtered.
Yield: 1.15 g of a white solid.

B. N-(2,2-Diphenylethyl)-S-(2-chlorophenyl)-thiourethane

The compound of Example 9A (1.15 g, 5 mmol) and 2,2-diphenylethylamine (0.99 g, 5 mmol) were reacted for 4 hours in 30 ml of DMF. The reaction mixture was partitioned between EtOAc and $H_2O$. The resultant organic layer was dried over $Na_2SO_4$, filtered and then concentrated in vacuo. The crude material was purified using flash chromatography (eluent of 25% EtOAc in hexanes) followed by recrystallization (hexanes/EtOAc).
Yield: 0.35 of a white solid (19%).
Elemental Analysis:
  Calcd: C, 68.56; H, 4.93; N, 3.81
  Found: C, 68.50; H, 5.10; N, 4.00
MS(FD): 367.0 (367.90)
$^1$H NMR ($d_6$-DMSO): 3.77 (dd, J=5.5,7.7 Hz, 2H); 4.25 (t, J=7.7 Hz, 1H); 7.13–7.38 (m, 11H); 7.44 (m, 1H); 7.56 (m, 2H); 8.53 (t, J=5.5 Hz, 1H)
IR (KBr): 3299, 1671, 1534, 1208 and 752 cm$^{-1}$.

EXAMPLE 10

N-(2,2-Diphenylethyl)-O-(2-chlorophenyl)-urethane

The compound was prepared substantially in accordance with the procedure detailed in Example 9 using 2-chlorophenol (0.64 m, 5 mmol) and triphosgene (1.48 g, 5 mmol) in 50 ml of $CH_2Cl_2$ followed by the addition of 2,2-diphenylethylamine (0.93 g, 5 mmol). The crude material was purified by recrystallization (hexanes/EtOAc).
Yield: 0.73 g of a white solid (44%).
Elemental Analysis:
  Calcd: C, 71.69; H, 5.16; N, 3.98;
  Found: C, 71.98; H, 5.35; N, 4.17.
MS(FD): 351.0 (351.84).
$^1$H NMR ($d_6$-DMSO) δ3.73 (dd, J=5.9,8.1 Hz, 2H); 4.28 (t, J=8.1 Hz, 1H); 7.13 (dd, J=1.5,7.7 Hz, 1H); 7.17–7.40 (m, 12H); 7.50 (dd, J=1.5,7.7 Hz, 1H); 8.05 (t, J=5.9 Hz, 1H)
IR (KBr): 3340, 1723, 1546, 1476, 1220 and 699 cm$^{-1}$.

EXAMPLE 11

A. 2-Chloroaniline hydrochloride

Hydrogen chloride (HCl (gas)) was slowly bubbled through a cold (0° C.) solution of 2-chloroaniline (4.10 ml, 39 mmol) in 50 ml of ethanol (EtOH), resulting in the formation of a white precipitate which was isolated by filtration.
Yield: 4.47 g of a pink solid (70%).

B. 2,2-Diphenylethylcyanamide

A cold (0° C.) solution of 2,2-diphenylethylamine (3.36 g, 17.0 mmol) in 50 ml of $Et_2O$, was treated with a solution of cyanogen bromide (1.15 g, 10.9 mmol) in 10 ml of $Et_2O$, under $N_2$, resulting in the formation of a white precipitate. This precipitate was removed by filtration and the filtrate was concentrated in vacuo.
Yield: 1.91 g of a dark yellow oil (79%).
$^1$H NMR ($d_6$-DMSO): δ3.61 (m, 2H) 4.10 (t, 1H), 6.81 (t, 1H), 7.10–7.38 (m, 10H).

C. N-(2-Chlorophenyl)-N'-(2,2-diphenylethyl)-guanidine

A solution of the compound of Example 11B (1.80 g, 8 mmol) in 40 ml of chlorobenzene was treated with the compound of Example 11A (1.14 g, 7 mmol), under $N_2$. The reaction mixture was stirred at 120–130° C. for 2 hours and then stored at 4° C. overnight resulting in a white precipitate. This precipitate was removed by filtration, treated with $NaHCO_3$ and extracted with EtOAc. The EtOAc solution was dried over $Na_2SO_4$, filtered and concentrated in vacuo.
Yield: 1.78 g of a white solid (73%).
Elemental Analysis:
  Calcd: C, 72.09; H, 5.76; N, 12.01
  Found: C, 71.80; H, 5.81; N, 11.77
MS(FD): 349 (349.87).
$^1$H NMR ($d_6$-DMSO): δ3.81 (t, J=5.9 Hz, 2H); 3.92 (m, 1H); 4.54 (t, J=7.7 Hz, 1H); 4.90 (s, 2H); 5.48 (t, J=5.5 Hz, 1H); 6.84 (d, J=7.7 Hz, 2H); 7.12 (m, 1H); 7.16–7.23 (m, 2H); 7.25–7.37 (m, 8H).
IR (KBr): 3456, 3278, 3093, 1623, 1583 and 702 cm$^{-1}$.

EXAMPLE 12

A. 2-Phenyl-2-(pyrid-2-yl)acetonitrile

To a cold (0° C.) solution of 2-chloropyridine (4.8 mL, 50 mmol) and benzyl cyanide (5.8 ml, 50 mmol) in 120 ml of DMF, was added with potassium t-butoxide (11.2 g, 100 mmol), under $N_2$. The reaction mixture was reacted for 3 hours and then partitioned between EtOAc and $H_2O$. The resulting layers were separated and the EtOAc layer was washed sequentially with $NaHCO_3$ and brine, dried over $Na_3SO_4$, filtered and concentrated in vacuo. The crude material was purified by recrystallization (hexanes/EtOAc).
Yield: 4.58 g of a yellow solid (47%).
$^1$H NMR ($d_6$-DMSO): δ5.90 (s, 1H), 7.12–7.56 (m, 7H), 7.81 (m, 1H), 8.55 (d, 1H).

B. 2-Phenyl-2-(pyrid-2-yl)ethylamine

A mixture containing the compound of Example 12A (2.33 g, 12 mmol), 50 ml of EtOH, 5 ml of 5N HCl and 0.6 g of 5% palladium-on-carbon (Pd/C) was reacted for 3 hours at 60° C. at 60 psi. The reaction mixture was filtered and the filtrate was neutralized with sodium hydroxide (NaOH) and then concentrated in vacuo to provide an oil. This oil was redissolved in EtOAc and washed sequentially with $NaHCO_3$ and brine, dried over $Na_2SO_4$, filtered and then concentrated in vacuo.
Yield: 1.21 g of a yellow oil (51%).
$^1$H NMR ($d_6$-DMSO): δ1.28 (br. m, 2H), 3.09 (m, 1H), 3.32 (m, 1H), 4.08 (t, 1H), 7.05–7.40 (m, 7H), 7.64 (t, 1H), 8.50 (d, 1H).

C. N-(2-Chlorophenyl)-N'-[2-phenyl-2-(pyrid-2-yl)-ethyl]-urea

The compound was prepared substantially in accordance with the procedure detailed in Example 1, using the compound of Example 12B (0.74 g, 3.7 mmol) and 2-chlorophenylisocyanate (0.45 ml, 3.7 mmol) in 15 ml of DMF. The crude material was purified using flash chromatography (eluent of 25% EtOAc in hexanes).
Yield: 0.66 g of a white solid (50%).
Elemental Analysis:
  Calcd: C, 68.28; H, 5.16; N, 11.94;
  Found: C, 68.45; H, 5.33; N, 11.86.
MS(FD): 351 (351.84).
$^1$H NMR ($d_6$-DMSO): δ3.80 (m, 1H); 3.92 (m, 1H); 4.34 (t, J=7.4 Hz, 1H); 6.93 (m, 1H); 7.01 (t, J=5.5 Hz, 1H); 7.16–7.40 (m, 9H); 7.72 (m, 1H); 8.04 (s, 1H); 8.14 (dd, J=1.5,8.5 Hz, 1H); 8.60 (d, J=4.0 Hz, 1H)
IR (KBr): 3330, 1645, 1549, 1442 and 751 cm$^{-1}$.

EXAMPLE 13

N-(2-Chlorophenyl)-N'-[2-phenyl-2-(pyrid-2-yl)-ethyl]-urea hydrochloride

The compound was prepared substantially in accordance with the procedure detailed in Example 11 using the compound of Example 12C (0.66 g, 1.9 mmol) and an excess of HCl (gas) in EtOH. Crystallization was aided by concentrating the EtOH solution and adding Et$_2$O.
Yield: 0.37 g of a yellow solid (51%).
Elemental Analysis:
  Calcd: C, 61.87; H, 4.93; N, 10.82; Cl, 18.26;
  Found: C, 61.34; H, 5.02 N, 10.83; Cl, 17.62.
MS(FD): 352 (388.30).
$^1$H NMR (d$_6$-DMSO): δ3.88 (m, 1H); 4.03 (m, 1H); 4.61 (t, J=7.7 Hz, 1H); 6.94 (m, 1H); 7.18–7.47 (m, 8H); 7.36 (m, 3H); 7.64 (m, 1H): 7.85 (m, 1H); 8.06 (s, 1H); 8.10 (dd, J=1.5,8.5 Hz, 1H); 8.20 (m, 1H); 8.74 (d, J=5.5 Hz, 1H)
IR (KBr): 3269, 3224, 2543, 1528 and 1227 cm$^{-1}$.

EXAMPLE 14

A. 2-Phenyl-2-(pyrid-3-yl)-acetonitrile

The compound was prepared substantially in accordance with the procedure in Example 12A, using 3-chloropyridine (9.5 ml, 100 mmol), benzyl cyanide (11.6 ml, 100 mmol) and potassium t-butoxide (22.4 g, 200 mmol) in 200 ml of DMF.
Yield: 2.03 g of an orange solid (10%).
$^1$H NMR (d$_6$-DMSO): δ5.90 (s, 1H), 7.15–7.50 (m, 6H), 7.80 (dd, 1H), 8.52 (d, 1H), 8.64 (s, 1H).

B. 2-Phenyl-2-(pyrid-3-yl)ethylamine

The compound was prepared substantially in accordance with the procedure in Example 12B, using the compound of Example 14A (2.0 g, 10.3 mmol), 95 ml of EtOH, 4 ml of 5N HCl and 5% Pd/C (2.0 g).
Yield: 0.75 g of a yellow oil (37%).
$^1$H NMR (d$_6$-DMSO): δ3.15 (d, 2H), 3.95 (t, 1H), 7.05–7.38 (m, 6H), 7.66 (d, 1H), 8.37 (d, 1H), 8.50 (s, 1H).

C. N-(2-Chlorophenyl)-N'-[2-phenyl-2-(pyrid-3-yl)ethyl]-urea

The compound was prepared substantially in accordance with the procedure detailed in Example 12C, using the compound of Example 14B (0.75 g, 3.8 mmol) and 2-chlorophenylisocyanate (0.5 mg, 3.8 mmol) in 30 ml of DMF.
Yield: 23.7 mg of a pale yellow solid (2%).
Elemental Analysis:
  Calcd: C, 68.28; H, 5.16; N, 11.94;
  Found: C, 65.58; H, 5.05; N. 11.47.
MS(FD): 352 (351.84).
$^1$H NMR (d$_6$-DMSO): δ3.82 (t, J=5.9 Hz, 2H); 4.26 (t, J=7.7 Hz, 1H); 6.94 (m, 1H); 7.06 (t, J=5.9 Hz, 1H); 7.23 (m, 2H); 7.31–7.42 (m, 6H); 7.78 (m, 1H); 8.03 (s, 1H); 8.14 (dd, J=1.5,8.1 Hz, 1H); 8.43 (dd, J=1.5,4.8 Hz, 1H); 8.60 (d, J=1.8 Hz, 1H)
IR (KBr): 3354, 3280, 1648, 1260 and 700 cm$^{-1}$.

EXAMPLE 15

A. 4-Chloropyridine

4-Chloropyridine hydrochloride was dissolved in methanol, and treated with excess NaHCO$_3$. The reaction mixture was concentrated in vacuo, dissolved in EtOAc and filtered. The filtrate was then concentrated in vacuo.
Yield: 3.26 g (8.7 mmol).

B. 2-Phenyl-2-(pyrid-4-yl)acetonitrile

The compound was prepared substantially in accordance with the procedure detailed in Example 12A, using the compound of Example 15A, benzyl cyanide (3.3 ml, 28.7 mmol) and potassium t-butoxide (6.44 g, 57.4 mmol) in 60 ml of DMF.
Yield: 2.92 g of an orange solid (52%).
$^1$H NMR: (d$_6$-DMSO): δ5.89 (s, 1H) , 7.20–7.45 (m, 7H) , 8.58 (d, 2H).

C. 2-Phenyl-2-(pyrid-4-yl)ethylamine

The compound was prepared substantially in accordance with the procedure detailed in Example 12B, using the compound of Example 15B (2.66 g, 13.6 mmol), 100 ml of EtOH, 15 ml of ammonia and Rainey nickel catalyst (0.35 g). The reaction was carried out for 8 hours at 80° C. and 500 psi.
Yield: 1.45 g of a yellow oil (54%).
$^1$H NMR (d$_6$-DMSO): δ3.15 (dd, 2H), 3.94 (t, 1H), 7.09–7.38 (m, 7H), 8.42 (d, 2H).

D. N-(2-Chlorophenyl)-N'-[2-phenyl-2-(pyrid-4-yl)ethyl]-urea

The compound was prepared substantially in accordance with the procedure detailed in Example 1, using the compound of Example 15C (1.37 g, 6.9 mmol) and 2-chlorophenylisocyanate (0.9 ml, 6.9 mmol) in 5 ml of DMF.
Yield: 1.23 g of a pale yellow solid (51%).
Elemental Analysis:
  Calcd: C, 68.28; H, 5.16; N, 11.94;
  Found: C, 68.43; H, 5.15; N, 12.16.
MS(FD): 351 (351.84).
$^1$H NMR (d$_6$-DMSO): δ3.81 (m, 2H); 4.23 (t, J=8.1 Hz, 1H); 6.94 (m, 1H); 7.05 (t, J=5.9 Hz, 1H); 7.18–7.42 (m, 9H); 8.03 (s, 1H); 8.14 (dd, J=1.5,8.5 Hz, 1H); 8.50 (d, J=5.5 Hz, 2H).
IR (KBr): 3316, 1698, 1532, 1206 and 760 cm$^{-1}$.

EXAMPLE 16

N-(2-Chlorophenyl)-N'-[2-phenyl-2-(pyrid-4-y1)-ethyl]-urea hydrochloride

The compound was prepared substantially in accordance with the procedure detailed in Example 11A, using HCl (gas) and the compound of Example 15D (1.23 g, 3.5 mmol) in EtOH. Crystallization was aided by concentrating the EtOH solution and adding Et$_2$O.
Yield: 0.93 g of a pale yellow solid (68%).
Elemental Analysis:
  Calcd: C, 61.87; H, 4.93; N, 10.82; Cl, 18.26;
  Found: C, 61.63; H, 4.91; N, 10.68; Cl, 18.54.
MS(FD): 351.2 (388.30).
$^1$H NMR (d$_6$-DMSO): δ3.60 (br.5, 1H); 3.85 (m, 1H); 3.97 (m, 1H); 4.56 (t, J=7.4 Hz, 1H); 6.95 (m, 1H); 7.15–7.48 (m, 8H); 7.94–8.13 (m, 3H); 8.82 (d, J=4.8 Hz, 2H).
IR (KBr): 3358, 3291, 3038, 2438, 1651, 1546 and 748 cm$^{-1}$.

EXAMPLE 17

A. 2-Phenyl-2-(quinol-2-yl)acetonitrile

The compound was prepared substantially in accordance with the procedure detailed in Example 12A, using 2-chloroquinoline (5.0 g, 30.6 mmol), benzyl cyanide (3.5 ml, 30.6 mmol) and potassium t-butoxide (6.87 g, 61.2 mmol) in 40 ml of DMF.
Yield: 4.5 g of an orange solid (60%).
$^1$H NMR (d$_6$-DMSO): δ6.12 (s, 1H), 7.22–7.63 (m, 7H), 7.75 (t, 1H), 7.91 (d, 1H), 8.03 (d, 1H), 8.35 (d, 1H).

B. 2-Phenyl-2-(6,7,8,9-tetrahydroquinol-2-yl) ethylamine

The compound was prepared substantially in accordance with the procedure detailed in Example 12B, using the compound of Example 17A (2.1 g, 8.6 mmol), 75 ml of EtOH, 3.6 ml of 5N HCl and 5% Pd/C (0.53 g).
Yield: 2.04 g of a yellow oil (96%).
$^1$H NMR (d$_6$-DMSO): δ1.65 (m, 2H), 1.72 (m, 2H), 2.60 (t, 2H), 2.77 (t, 2H), 3.08 (m, 1H), 3.31 (m, 1H), 4.00 (t, 1H), 6.90 (d, 1H), 7.05–7.35 (m, 6H).

C. N-(2-Chlorophenyl)-N'-[2-phenyl-2-(6,7,8,9-tetrahydroquinol-2-yl)-ethyl]-urea The compound was prepared substantially in accordance with the procedure detailed in Example 12B, using the compound of Example 17B (2.04 g, 8.2 mmol) and 2-chlorophenyl isocyanate (1.0 ml, 8.2 mmol) in 25 ml of DMF.
Yield: 93 mg of a pale yellow solid (93%).
Elemental Analysis:
    Calcd: C, 71.01; H, 5.96; N, 10.35;
    Found: C, 70.97; H, 5.91; N, 10.38.
MS(FD): 405 (405.91).
$^1$H NMR (d$_6$-DMSO): δ1.78 (m, 4H); 2.69 (t, J=6.3 Hz, 2H); 2.84 (t, J=6.3 Hz, 2H); 3.74 (m, 1H); 3.87 (m, 1H); 4.22 (t, J=7.7 Hz, 1H); 6.94 (m, 2H); 7.07 (d, J=8.1 Hz, 1H); 7.15–7.41 (m, 8H); 8.04 (s, 1H); 8.14 (dd, J=1.5,8.5 Hz, 1H)
IR (KBr): 3332, 2938, 1654, 1538, 1439 and 750 cm$^{-1}$.

EXAMPLE 18

A. 2-Phenyl-2-(quinol-2-yl)methylamine

The compound was isolated from Example 17B.

B. N-(2-Chlorophenyl)-N'-[2-phenyl-2-(quinol-2-yl]-ethylurea

The compound was prepared substantially in accordance with the procedure detailed in Example 12B, using the compound of Example 18A (0.7 g, 2.8 mmol) and 2-chlorophenyl isocyanate (0.4 ml, 3.0 mmol) in 10 ml of DMF.
Yield: 0.24 g of a pale yellow solid (21%).
Elemental Analysis:
    Calcd: C, 71.73; H, 5.02; N, 10.45;
    Found: C, 72.07; H, 5.18; N, 9.71.
MS(FD): 401.4 (401.90).
$^1$H NMR (d$_6$-DMSO): δ3.90 (m, 1H); 4.10 (m, 1H); 4.55 (t, J=6.6 Hz, 1H); 6.93 (m, 1H); 7.06 (t, J=5.9 Hz, 1H); 7.22 (t, J=7.4 Hz, 2H); 7.27–7.43 (m, 5H); 7.50 (d, J=8.5 Hz, 1H); 7.59 (t, J=7.7 Hz, 1H); 7.78 (t, J=8.1 Hz, 1H); 7.95 (d, J=8.1 Hz, 1H); 8.08 (m, 2H); 8.14 (dd, J=1.1,8.5 Hz, 1H); 8.29 (d, J=8.5 Hz, 1H)
IR (KBr): 3323, 1652, 1539, 1439 and 749 cm$^{-1}$.

EXAMPLE 19

A. Cyclohexyl acetonitrile

A solution of sodium cyanide (2.77 g, 56.5 mmol) in 70 ml of DMF was treated with cyclohexyl bromide (7.9 ml, 56.5 mmol), under N$_2$. The reaction mixture was reacted for 48 hours and then partitioned between EtOAc and H$_2$O. The resultant layers were separated and the organic layer was concentrated in vacuo. The crude material was purified using flash chromatography (eluent of 5% EtOAc in hexanes).
Yield: 5.0 g of a clear liquid (72%).
$^1$H NMR (d$_6$-DMSO): δ0.65–1.30 (m, 5H), 1.35–1.80 (m, 6H), 2.38 (d, 2H).

B. 2-Cyclohexyl-2-(pyrid-2-yl)-acetonitrile

The compound was prepared substantially in accordance with the procedure detailed in Example 12A, using the compound of Example 19A (4.0 g, 32.5 mmol), 2-chloropyridine (3.1 ml, 32.5 mmol) and lithium bis (trimethylsilyl)amide (1.0M in THF, 39 ml, 39 mmol) in 15 ml of THF.
Yield: 3.74 g of a clear liquid (58%).
$^1$H NMR (d$_6$-DMSO): δ1.00–1.30 (m, 5H), 1.45–1.80 (m, 5H), 1.95 (m, 1H), 4.24 (d, J=7.0 Hz, 1H), 7.32–7.46 (m, 2H), 7.85 (m, 1H), 8.60 (d, J=4.8 Hz, 1H).
IR (neat): 2928, 2854 and 2242 cm$^{-1}$.
MS(FD): 201.
Elemental Analysis:
    Calcd: C, 75.37; H: 7.57; N: 12.98;
    Found: C, 77.96; H, 8.05; N, 13.99.

C. 2-Cyclohexyl-2-(pyrid-2-yl)-ethylamine

The compound was prepared substantially in accordance with the procedure detailed in Example 12B, using the compound of Example 19B, 50 ml of EtOH, 5 ml of 5N HCl and 5% Pd/C (0.25 g).
Yield: 1.20 g of a yellow oil (59%).
$^1$H NMR (d$_6$-DMSO): δ0.50–1.30 (m, 6H), 1.30–1.90 (m, 5H), 2.35–3.10 (m, 3H), 7.00–7.20 (m, 2H), 7.63 (t, 1H), 8.48 (d, 1H).

D. N-(2-Chlorophenyl)-N'-[2-cyclohexyl-2-(pyrid-2-yl)-ethyl]urea

The compound was prepared substantially in accordance with the procedure detailed in Example 11, using the compound of Example 19C (1.44 g, 5.58 mmol) and 2-chlorophenyl isocyanate (0.67 ml, 5.58 mmol) in 15 ml of DMF.
Yield: 1.02 of a tan solid (51%).
Elemental Analysis:
    Calcd: C, 67.12; H, 6.76; N, 11.74;
    Found: C, 66.89; H, 6.67; N, 11.54.
MS(FD): 357 (357.89).
$^1$H NMR (d$_6$-DMSO): δ0.73–1.36 (m, 6H); 1.45–1.80 (m, 4H); 1.86 (m, 1H); 2.76 (m, 1H); 3.21 (m, 1H); 3.62 (m, 1H); 6.74 (t, J=4.8 Hz, 1H); 6.92 (m, 1H); 7.21 (m, 3H); 7.35 (dd, J=1.5, 8.1 Hz, 1H); 7.71 (m, 1H); 7.97 (s, 1H); 8.10 (d, J=8.5 Hz, 1H); 8.56 (d, J=5.2 Hz, 1H).
IR (KBr): 3351, 2925, 1657, 1554, 1438 and 749 cm$^{-1}$.

EXAMPLE 20

N-(2-Chlorophenyl)-N'-[2-cyclohexyl-2-(pyrid-2-yl) ethyl]urea hydrochloride

The compound was prepared substantially in accordance with the procedure detailed in Example 11A, using HCl (gas) and the compound of Example 15C (1.23 g, 3.5 mmol) in EtOH. The resultant crystals were washed with EtOAc.
Yield: 0.85 g of a white solid (76%).

Elemental Analysis:
  Calcd: C, 60.92; H, 6.39; N, 10.66; Cl, 17.98;
  Found: C, 60.76; H, 6.35; N, 10.47; Cl, 17.76.
MS(FD): 357.2 (394.35).
$^1$H NMR (d$_6$-DMSO): δ0.76–1.36 (m, 6H); 1.48–1.80 (m, 4H); 1.96 (m, 1H); 3.10 (m, 1H); 3.30 (m, 1H); 3.72 (m, 1H); 6.93 (m, 1H); 7.02 (br.m, 1H); 7.21 (m, 1H); 7.36 (dd, J=1.5,8.1 Hz, 1H); 7.81 (br.m, 2H); 7.95 (s, 1H); 8.01 (d, J=8.5 Hz, 1H); 8.36 (br.m, 1H); 8.79 (d, J=4.8 Hz, 1H).
IR (KBr): 3232, 2919, 2585, 1706, 1521 and 768 cm$^{-1}$.

EXAMPLE 21

A. Cyclohexylphenylacetamide

A suspension of cyclohexylphenylacetic acid (4.00 g, 18.3 mmol) in 25 ml of toluene was heated to 35° C. and treated with oxalyl chloride (2.3 ml, 25.7 mmol). The reaction mixture was stirred at 35–40° C. for 22 hours, cooled to room temperature and then concentrated in vacuo to provide a yellow oil. This oil was dissolved in 50 ml of Et$_2$O and cooled to 0° C. Ammonia was bubbled through the resultant solution for 15 minutes which resulted in the formation of a white precipitate. This precipitate was isolated by filtration, washed with Et$_2$O and then purified by recrystallization (EtOH/H$_2$O).
Yield: 1.52 g of a white solid (38%).
$^1$H NMR (d$_6$-DMSO): δ0.66 (m, 1H), 1.15 (m, 5H), 1.56 (m, 2H), 1.80 (m, 3H), 3.06 (d, J=10.7 Hz, 1H), 6.77 (br.s, 1H), 7.15–7.33 (m, 5H), 7.46 (br.s, 1H).
IR (KBr): 3409, 3186, 2919, 2849, 1653, 696.
MS(FD): 217.
Elemental Analysis:
  Calcd: C, 77.26; H, 8.97; N, 6.61;
  Found: C, 77.38; H, 8.81; N, 6.44.

B. 2-Cyclohexyl-2-phenyl-ethylamine

To a refluxing suspension of the compound of Example 21A (1.24 g, 5.7 mmol) in 0.3 ml of THF, was added a borane-tetrahydrofuran complex (1.0M in THF, 11.4 ml, 11.4 mmol), dropwise. The reaction mixture was refluxed overnight and cooled to room temperature, followed by the dropwise addition of 1.5 ml of MeOH. After 6 hours, a cold solution of saturated ethereal HCl was poured into the MeOH solution which resulted in the formation of a precipitate. This precipitation was isolated by filtration and then partitioned between 1.0N NaOH and CH$_2$Cl$_2$. The resultant layers were separated, and the organic layer was dried over Na$_2$SO$_4$, filtered, and then concentrated in vacuo.
Yield: 0.51 g of a clear oil (44%).
$^1$H NMR (d$_6$-DMSO): δ1.25 (br.s, 2H), 3.12 (d, 2H), 3.89 (t, 1H), 7.05–7.35 (m, 5H).

C. N-(2-Chlorophenyl)-N'-(2-cyclohexyl-2-phenylethyl)-urea

The compound was prepared substantially in accordance with the procedure detailed in Example 1, using the compound of Example 21B (0.5 g, 2.5 mmol) and 2-chlorophenyl isocyanate (0.3 ml, 2.7 mmol) in 15 ml of DMF.
Yield: 0.54 g of a white solid (62%).
Elemental Analysis:
  Calcd: C, 70.67; H, 7.06; N, 7.85;
  Found: C, 70.94; H, 7.13; N, 8.09.
MS(FD): 356 (356.90).
$^1$H NMR (d$_6$-DMSO): δ0.76 (m, 1H); 0.84–1.32 (m, 4H); 1.40 (m, 1H); 1.57 (m, 3H); 1.70 (m, 1H); 1.86 (m, 1H); 2.58 (m, 1H); 3.26 (m, 1H); 3.67 (m, 1H): 6.73 (t, J=4.8 Hz, 1H); 6.92 (m, 1H); 7.15–7.39 (m, 7H); 7.99 (s, 1H); 8.11 (d, J=8.1 Hz, 1H).
IR (KBr): 3356, 2925, 2853, 1661, 1553, 1437 and 747 cm$^{-1}$.

EXAMPLE 22

Dicyclohexylacetamide

The compound was prepared substantially in accordance with the procedure detailed in Example 21A, using dicyclohexylacetic acid (4.00 g, 17.8 mmol) and oxalyl chloride (2.2 ml, 25.2 mmol) in 25 ml of toluene to provide a clear oil. This oil was then dissolved in Et$_2$O and treated with ammonia.
Yield: 2.98 g of a white solid (75%).
$^1$H NMR (d$_6$-DMSO): δ0.80–1.29 (m, 11H), 1.44–1.73 (m, 11H), 1.80 (t, J=6.6 Hz, 1H), 6.64 (br.s, 1H), 7.12 (br.s, 1H).
IR (KBr): 3428, 3209, 2933, 2849, 1654, 1448 and 602 cm$^{-1}$.
MS(FD): 224.
Elemental Analysis:
  Calcd: C, 75.12; H, 11.21; N, 6.56;
  Found: C, 75.28; H, 11.28; N, 6.27.

B. 2,2-Dicyclohexylethylamine

The compound was prepared substantially in accordance with the procedure detailed in Example 21B, using a refluxing mixture of the compound of Example 22A (2.49 g, 11.1 mmol) in 2.0 ml of THF and a borane-methyl sulfide complex (2.0M in THF, 11.2 ml, 22.3 mmol) which was treated consecutively with MeOH, ethereal HCl and NaOH.
Yield: 1.44 g of a clear oil (62%).
$^1$H NMR (d$_6$-DMSO): δ0.80–1.80 (m, 23H), 2.50 (m, 2H).

C. N-(2-Chlorophenyl)-n'-(2,2-dicyclohexylethyl)-urea

The compound was prepared substantially in accordance with the procedure detailed in Example 1, using the compound of Example 22B (1.44 g, 6.9 mmol) and 2-chlorophenyl isocyanate (0.9 ml, 7.6 mmol) in 25 ml of DMF.
Yield: 2.13 g of a white solid (85%).
Elemental Analysis:
  Calcd: C, 69.50; H, 8.61; N, 7.72;
  Found: C, 69.20; H, 8.55; N, 7.63.
MS(FD): 362, 725 (362.95).
$^1$H NMR (d$_6$-DMSO): δ1.00–1.80 (m, 23H); 3.13 (m, 2H); 6.79 (m, 1H); 6.93 (t, J=7.4 Hz, 1H); 7.22 (t, J=7.4 Hz, 1H); 7.39 (d, J=8.5 Hz, 1H); 8.03 (s, 1H); 8.17 (d, J=9.2 Hz, 1H).
IR (KBr): 3320, 2928, 2851, 1645, 1567 and 746 cm$^{-1}$.

EXAMPLE 23

A. 9-Fluorene carboxamide

The compound was prepared substantially in accordance with the procedure detailed in Example 21A, using 9-fluorenecarboxylic acid (6.00 g, 28.5 mmol) and oxalyl chloride (3.5 ml, 39.9 mmol) in 30 ml of toluene to provide a clear oil that was dissolved in Et$_2$O and treated with ammonia.
Yield: 5.48 g of a white solid (96%).
$^1$H NMR (d$_6$-DMSO): δ4.78 (s, 1H), 7.10–7.45 (m, 5H), 7.57 (d, 2H), 7.83 (m, 3H).

B. 9H-Fluoren-9-ylmethylamine hydrochloride

The compound was prepared substantially in accordance with the procedure detailed in Example 21B, using a refluxing mixture of the compound of Example 23A (3.14 g, 15.0 mmol) in 6.0 ml of THF and a borane-methyl sulfide complex (2.0M in THF, 11.0 ml, 22.0 mmol) which was treated consecutively with MeOH and ethereal HCl.
Yield: 1.46 g of a white solid (42%).
$^1$H NMR (d$_6$-DMSO): δ3.30 (m, 2H), 4.36 (t, 1H), 7.25–7.55 (m, 4H), 7.75 (d, 2H), 7.90 (d, 2H), 8.38 (br.s, 2H).

C. 9H-Fluoren-9-ylmethylamine

A solution of the compound of Example 23B (1.46 g, 6.3 mmol) in 25 ml of MeOH was treated with NaHCO$_3$.
Yield: 0.4 g (2.1 mmol).

D. N-(2-Chlorophenyl)-N'-(9H-fluoren-9-ylmethyl)-urea

The compound was prepared substantially in accordance with the procedure detailed in Example 1, using the compound of Example 23C (0.4 g, 2.1 mmol) and 2-chlorophenyl isocyanate (0.3 ml, 2.5 mmol) in 10 ml of DMF. The crude material was purified using flash chromatography (eluent of 25% EtOAc in hexanes).
Yield: 0.16 g of a white solid (22%).
Elemental Analysis:
  Calcd: C, 72.31; H, 4.91; N, 8.03;
  Found: C, 72.59; H, 5.17; N, 8.30.
MS(FD): 348 (348.84).
$^1$H NMR (d$_6$-DMSO): δ3.67 (t, J=6.3 Hz, 2H); 4.15 (t, J=6.3 Hz, 1H); 6.95 (m, 1H); 7.08 (t, J=5.5 Hz, 1H); 7.23 (m, 1H); 7.32–7.44 (m, 5H); 7.67 (d, J=7.0 Hz, 2H); 7.91 (d, J=7.0 Hz, 2H) ; 8.11 (dd, J=1.1,8.5 Hz, 1H) ; 8.16 (s, 1H)
IR (KBr): 3329, 1642, 1586 and 739 cm$^{-1}$.

EXAMPLE 24

A. 1,2,3,4,4a,9a-Hexahydrofluorene-9-carboxylic acid

A mixture of 9-fluorenecarboxylic acid (5.0 g, 23.8 mmol) and platinum oxide (0.5 g) in 200 ml of acetic acid were reacted for 8 hours at room temperature and 45 psi. The reaction mixture was filtered and the filtrate concentrated in vacuo to provide a white solid which was purified using flash chromatography (eluent of CHCl$_3$) followed by recrystallization (EtOH/H$_2$O).
Yield: 0.84 g of a white solid (16%).
$^1$H NMR (d$_6$-DMSO): δ0.65–1.94 (m, 7H), 2.26 (m, 1H), 2.70 (m, 1H), 3.17 (m, 1H), 3.94 (d, J=5.9 Hz, 1H), 7.12–7.27 (m, 3H), 7.42 (d, J=6.6 Hz, 1H), 12.35 (br.s, 1H).
IR (KBr): 3439, 3022, 2925, 1693 and 739 cm-$^1$.
MS(FD) 216.1.

B.

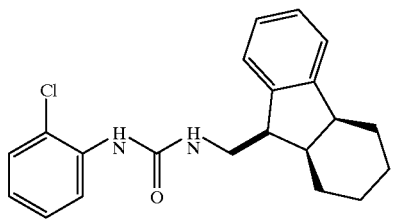

The compound was prepared substantially in accordance with the procedure detailed in Example 21A–C. The crude material was purified using flash chromatography (eluent of 20% EtOAc in hexanes) to provide a white solid. Elemental Analysis:
  Calcd: C, 71.08; H, 6.53; N, 7.89;
  Found: C, 71.11; H, 6.56; N, 7.71.
MS(FD): 354.2 (354.88).
$^1$H NMR (d$_6$-DMSO): δ0.71 (m, 1H); 1.01 (m, 1H); 1.17 (m, 1H); 1.52 (m, 3H); 1.74 (m, 1H); 2.29 (m, 1H); 3.17 (m, 4H); 3.80 (m, 1H); 6.95 (t, J=7.7 Hz, 1H); 7.11–7.29 (m, 6H); 7.42 (d, J=8.1 Hz, 1H); 8.12 (s, 1H); 8.21 (d, J=8.5 Hz, 1H)
IR (KBr) 3322, 2930, 2855, 1644, 1561, 1439 and 742 cm$^{-1}$.

EXAMPLE 25

A. Perhydrofluorene-9-carboxylic acid

The compound was prepared substantially in accordance with the procedure detailed in Example 24A, using 9-fluorenecarboxylic acid (5.85 g, 27.8 mmol), 200 ml of acetic acid and platinum oxide (3.0 g). The crude material was purified by recrystallization (EtOH/H$_2$O).
Yield: 4.25 g of a white solid (68%).
$^1$H NMR (d$_6$-DMSO): δ1.04 (d, J=6.3 Hz, 1H), 1.10–1.75 (m, 15H), 2.02 (m, 2H), 2.16 (m, 2H), 2.92 (t, J=8.5 Hz, 1H), 11.80 (br.s, 1H).
IR (KBr): 2934, 2864, 1684 and 722 cm$^{-1}$.
MS(FD): 222.0.
Elemental Analysis:
  Calcd: C, 75.90; H: 9.92;
  Found: C, 75.63; H, 9.97.

B. N-(2-Chlorophenyl)-N'-(perhydrofluoren-9-ylmethyl)-urea

The compound was prepared substantially in accordance with the procedure detailed in Example 21A–C.
Elemental Analysis:
  Calcd: C, 69.88; H, 8.10; N, 7.76;
  Found: C, 70.14; H, 7.95; N, 8.00.
MS(FD): 360.2 (360.93).
$^1$H NMR (d$_6$-DMSO): δ1.10–1.75 (m, 19H); 1.87 (m, 2H); 3.15 (m, 2H); 6.95 (m, 2H); 7.22 (t, J=7.4 Hz, 1H); 7.38 (d, J=8.1 Hz, 1H); 8.02 (s, 1H); 8.15 (d, J=8.5 Hz, 1H)
IR (KBr): 3356, 3304, 2925, 1647, 1558 and 739 cm$^{-1}$.

EXAMPLE 26

A. Dibenzosuber-5-yl chloride

A cold (0° C.) suspension of dibenzosuberol (9.88 g, 47.1 mmol) in 80 ml of CH$_2$Cl$_2$ was treated with thionyl chloride (4.2 ml, 57.6 mmol). The reaction mixture was reacted at room temperature for 2 days, under N$_2$ and then quenched with ice. The resultant layers were separated and the organic layer was washed consecutively with NaHCO$_3$ and brine, dried over Na$_2$SO$_4$, filtered and then concentrated in vacuo.
Yield: 6.71 g (62%).
$^1$H NMR (CDCl$_3$): δ3.00 (m, 4H), 6.18 (s, 1H), 7.10–7.45 (m, 8H).

B. Dibenzosuber-5-yl carbonitrile

To a solution of the compound of Example 26A (5.66, 24.7 mmol) in 175 ml of toluene, was added copper (I) cyanide. The reaction mixture was refluxed for 2 days and then quenched with 5% ammonium hydroxide and partitioned between EtOAc and H$_2$O. The resulting layers were separated and the organic layer was dried over Na$_2$SO$_4$, filtered and concentrated in vacuo. The crude material was purified using flash chromatography (eluent of 5% EtOAc in hexanes).
Yield: 1.87 g of an orange solid (35%).
$^1$H NMR (CDCl$_3$): δ3.20 (m, 4H), 6.05 (s, 1H), 7.10–7.35 (m, 6H), 7.47 (d, 2H).

C. Dibenzosuber-5-yl methylamine

The compound was prepared substantially in accordance with the procedure detailed in Example 19C, using the compound of Example 26B (1.2 g, 5.5 mmol), 30 ml of EtOH, 2.3 ml of 5N HCl and 5% Pd/C (0.3 g).
Yield: 0.58 g of a white solid (48%).
$^1$H NMR (d$_6$-DMSO): δ2.92 (m, 2H), 3.25 (m, 4H), 4.26 (t, 1H), 6.95–7.30 (m, 8H).

D.

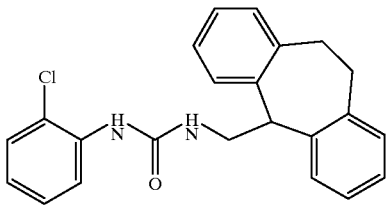

The compound was prepared substantially in accordance with the procedure detailed in Example 1, using the compound of Example 26C (0.58 g, 2.6 mmol) and 2-chlorophenyl isocyanate (0.3 ml, 2.6 mmol) in 10.5 ml of DMF. The crude material was purified by recrystallization (hexanes/EtOAc).
Yield: 15 mg of a white solid.
MS(FD): 376.2 (376.89).
$^1$H NMR (d$_6$-DMSO): δ3.00 (t, 2H); 3.24 (t, 2H); 3.72 (m, 2H); 4.27 (t, 1H); 6.92 (m, 2H); 7.10–7.22 (m, 9H); 7.36 (d, 1H); 8.00 (s, 1H); 8.10 (d, 1H).

EXAMPLE 27

A. 2,2-Diphenylethyl isocyanate

A suspension of triphosgene (0.78 g, 2.6 mmol) in 15 ml of CH$_2$Cl$_2$ was treated in small portions with 2,2-diphenylethylamine (1.54 g, 7.8 mmol) at 0° C., under N$_2$. The reaction mixture was stirred for 30 minutes and filtered. The filtrate was then concentrated in vacuo to provide a yellow oil.
Yield: 1.00 g (80%).

B. 2-Chlorobenzyl azide

A cold (0° C.) solution of sodium azide (1.45 g, 22.3 mmol) in 50 ml of DMF was treated with 2-chlorobenzyl chloride (2.4 ml, 18.6 mmol). The reaction mixture was stirred at room temperature for 2 days, under N$_2$ and then partitioned between EtOAc and H$_2$O. The resultant layers were separated and the organic layer was dried over Na$_2$SO$_4$, filtered and then concentrated in vacuo.
Yield: 2.65 g of an oil (85%)
$^1$H NMR (CDCl$_3$): δ4.50 (s, 2H), 7.20–7.38 (m, 2H), 7.38–7.50 (m, 2H).

C. 2-Chlorobenzylamine

A mixture containing the compound of Example 27B (2.65 g, 15.9 mmol) and platinum oxide (0.27 g) in 95 ml of EtOAc was reacted for 2 hours at room temperature and 60 psi. The reaction mixture was filtered and concentrated in vacuo to provide an oil which was dissolved in EtOAc, washed consecutively with NaHCO$_3$ and brine, dried over Na$_2$SO$_4$, filtered and then concentrated in vacuo.
Yield: 1.39 g of a yellow oil (62%).

D. N-(2-Chlorobenzyl)-n'-(2,2-diphenylethyl)-urea

The compound was prepared substantially in accordance with the procedure detailed in Example 1, using 2,2-diphenylethyl isocyanate (0.56 g, 2.5 mmol) and the compound of Example 27C (0.35 g, 2.5 mmol) in 15 ml of DMF for 30 minutes. The crude material was purified by recrystallization (hexanes/EtOAc).
Yield: 0.43 g of a white solid (47%).
Elemental Analysis:
 Calcd: C, 72.42; H, 5.80; N, 7.68;
 Found: C, 72.65; H, 5.91; N, 7.94.
MS(FD): 364 (364.88).
$^1$H NMR (d$_6$-DMSO): δ3.69 (dd, J=5.9,7.7 Hz, 2H); 4.15 (t, J=8.1 Hz, 1H); 4.23 (d, J=5.9 Hz, 2H); 6.00 (t, J=5.9 Hz, 1H); 6.39 (t, J=5.5 Hz, 1H); 7.12–7.43 (m, 14H).
IR (KBr): 3331, 1639, 1583, 1255 and 705 cm$^{-1}$.

EXAMPLE 28

A. 2-Chloro-3-methyl aniline

A mixture of 2-chloro-3-nitrotoluene (1.0 g, 5.8 mmol) and 5% platinum-on-carbon (0.1 g) in 25 ml of EtOH was reacted overnight at room temperature and 60 psi. The reaction mixture was filtered and the filtrate concentrated in vacuo to provide an oil. This oil was dissolved in EtOAc, washed with H$_2$O, dried over Na$_2$SO$_4$, filtered and then concentrated in vacuo.
Yield: 0.53 g of a yellow oil (64%).

B. 2-Chloro-3-methylphenyl isocyanate

The compound was prepared substantially in accordance with the procedure detailed in Example 27A, using the compound of Example 28A (0.25 g, 1.77 mmol), triphosgene (0.17 g, 0.59 mmol) and triethylamine (Et$_3$N) (0.25 ml, 1.77 mmol) in 10 ml of chlorobenzene.
Yield: 0.20 g of an orange oil (67%).

C. N-(2-Chloro-3-methylphenyl)-N'-(2,2-diphenylethyl)-urea

The compound was prepared substantially in accordance with the procedure detailed in Example 1, using the compound of Example 28B (0.20 g, 1.2 mmol) and 2,2-diphenylethylamine (0.24 g, 1.2 mmol) in 10 ml of DMF. The crude material was purified by recrystallization (hexanes/EtOAc).
Yield: 0.21 g of a white solid (48%).
Elemental Analysis:
 Calcd: C, 72.42; H, 5.80; N, 7.68;
 Found: C, 71.37; H, 5.84; N, 7.49.
MS(FD): 364.1 (364.88).
$^1$H NMR (d$_6$-DMSO): δ2.30 (s, 3H); 3.32 (s, 1H); 3.78 (dd, J=5.5,7.4 Hz, 2H); 4.19 (t, J=8.1 Hz, 1H); 6.91 (d, J=6.6 Hz, 1H); 7.04 (t, J=5.5 Hz, 1H); 7.11 (t, J=7.7 Hz, 1H); 7.17–7.38 (m, 9H); 8.00 (d, J=8.8 Hz, 1H); 8.02 (s, 1H)
IR (KBr): 3352, 3288, 1645, 1564, 1240 and 698 cm$^{-1}$.

EXAMPLE 29

A. 1-Phenyl-1-cyclohexane-methylamine

A mixture containing 1-phenyl-1-cyclohexane-carbonitrile (5.0 g, 27.0 mmol), 150 ml of EtOH, 35 ml of ammonia and 5% rhodium on alumina (1.0 g) was reacted for 12 hours at 80° C. and 500 psi. The mixture was filtered and the filtrate was concentrated in vacuo to provide an oil. This oil was dissolved in CH$_2$Cl$_2$, washed with brine, dried over Na$_2$SO$_4$, filtered and then concentrated in vacuo.
Yield: 4.59 g of a clear oil (90%).
$^1$H NMR (d$_6$-DMSO): δ1.10–2.20 (m, 11H), 2.02 (m, 2H), 2.52 (s, 2H), 7.20 (m, 11H), 7.35 (m, 2H), 7.45 (t, 1H), 7.51 (d, 1H).

B. N-(2-Chlorophenyl)-N'-(1-phenyl-1-cyclohexanemethyl)-urea

The compound was prepared substantially in accordance with the procedure detailed in Example 1, using the compound of Example 29A (4.59 g, 24.2 mmol) and 2-chlorophenyl isocyanate (3.2 ml, 26.6 mmol) in 25 ml of DMF. A portion of the crude product (4.72 g, 57%) was purified by recrystallization (hexanes/$CH_2Cl_2$) to provide a white solid.

Elemental Analysis:
    Calcd: C, 70.06; H, 6.76; N, 8.17;
    Found: C, 70.28; H, 6.91; N, 8.38.
MS(FD): 342 (342.87).
$^1$H NMR ($d_6$-DMSO): δ1.32 (m, 4H); 1.58 (m, 4H); 2.02 (m, 2H); 3.26 (d, J=5.9 Hz, 2H); 6.68 (t, J=5.9 Hz, 1H); 6.91 (m, 1H); 7.20 (m, 2H); 7.40 (m, 5H); 8.08 (m, 2H)
IR (KBr): 3352, 2933, 1646, 1544 and 756 $cm^{-1}$.

EXAMPLE 30

3-phenyl-3-cyclohexanepropanamide

A solution of 3-phenyl-3-cyclohexanepropanoic acid (0.5 g, 2.15 mmol) and oxalyl chloride (0.3 ml, 3.01 mmol) in 5 ml of toluene was stirred for 3 hours at 35–40° C. and then at room temperature overnight. The mixture was then concentrated in vacuo to provide a yellow oil which was dissolved in 5 ml of $CH_2Cl_2$, cooled to 0° C. and treated with 2-chloroaniline. The resultant mixture was stirred at 0° C. for 2 hours and filtered. The filtrate was then washed sequentially with 1.0N HCl, $NaHCO_3$ and brine, dried over $Na_2SO_4$, filtered and then concentrated in vacuo to provide a white solid (0.66 g, 92%). A portion of this solid was recrystallized (hexanes/$CH_2Cl_2$) to provide a white solid.

Elemental Analysis:
    Calcd: C, 73.78; H, 7.08; N, 4.10;
    Found: C, 74.00; H, 7.15; N, 4.30.
MS(FD): 341.1 (341.88).
$^1$H NMR ($d_6$-DMSO): δ1.20–1.70 (m, 8H); 1.86 (m, 2H); 1.97 (m, 2H); 2.09 (m, 2H); 7.18 (m, 2H); 7.27 (t, J=7.0 Hz, 1H); 7.36 (m, 4H); 7.44 (d, J=8.1 Hz, 1H); 7.56 (d, J=6.6 Hz, 1H); 9.38 (s, 1H).
IR (KBr): 3328, 2934, 2856, 1679, 1526 and 759 $cm^{-1}$.

EXAMPLE 31

A. 4-Cyano-4-phenylcyclohexanol

A cold (0° C.) solution of 4-cyano-4-phenylcyclohexanone (5.0 g, 25.1 mmol) in 30 ml of MeOH was treated with sodium borohydride (1.14 g, 30.1 mmol). The reaction mixture was stirred for 2 hours at room temperature and then concentrated in vacuo.

Yield: 3.76 g (74%).
$^1$H NMR ($d_6$-DMSO): δ1.40–2.10 (m, 9H), 3.50 (m, 1H), 4.80 (d, 1H), 7.25–7.60 (m, 5H).

B. 4-Aminomethyl-4-phenyl-cyclohexanol

The compound was prepared substantially in accordance with the procedure detailed in Example 29A, using the compound of Example 31A (3.71 g, 18.4 mmol), 150 ml of EtOH, 35 ml of ammonia and 5% rhodium on alumina (1.0 g). The reaction mixture was filtered and the filtrate was concentrated in vacuo to provide an oil which was dissolved in $CH_2Cl_2$, washed sequentially with $H_2O$ and brine, dried over $Na_2SO_4$, filtered and concentrated in vacuo.
Yield: 3.44 g (91%).
$^1$H NMR ($d_6$-DMSO): δ1.41 (m, 5H), 1.66 (m, 2H), 1.90 (m, 2H), 2.57 (s, 2H), 3.50 (m, 1H), 4.20 (br.s, 1H) and 7.10–7.40 (m, 5H).

C. N-(2-Chlorophenyl)-N'-[1-(1"-phenyl-cyclohexan-4'-ol)-methyl]-urea

The compound was prepared substantially in accordance with the procedure detailed in Example 1, using the compound of Example 31B (1.50 g, 7.3 mmol) and 2-chlorophenyl isocyanate (1.0 ml, 8.0 mmol) in 12 ml of DMF. The crude material was purified by recrystallization (hexanes/EtOAc).

Yield: 1.67 g of a white solid (64%).
Elemental Analysis:
    Calcd: C, 66.94; H, 6.46; N, 7.81;
    Found: C, 66.74; H, 6.40; N, 7.60.
MS:(FD): 354.2 (354.88).
$^1$H NMR ($d_6$-DMSO): δ1.53 (m, 4H); 1.73 (m, 2H); 1.96 (m, 2H); 3.52 (m, 1H); 4.49 (d, J=3.7 Hz, 1H); 6.61 (m, 1H); 6.92 (t, J=8.5 Hz, 1H); 7.21 (m, 2H); 7.38 (m, 5H); 8.09 (m, 2H)
IR (KBr): 3306, 2934, 1678, 1558, 1061 and 747 $cm^{-1}$.

EXAMPLE 32

N-(2-Chlorophenyl)-N'-[1-(1"-phenyl-cyclohexan-4'-one)-methyl]-urea

A mixture of the compound of Example 31C (0.25 g, 0.7 mmol), pyridinium chlorochromate (0.6 g, 2.8 mmol) and 3 Å molecular sieves (1.2 g) in 4 ml of $CH_2Cl_2$, under $N_2$, was stirred for 1 hour. The reaction mixture was cooled to 0° C. and treated with $NaHCO_3$ and filtered. The filtrate was partitioned between $CH_2Cl_2$ and $H_2O$. The resultant layers were separated and the organic layer was filtered and concentrated in vacuo. The crude material was purified using flash chromatography (eluent of 1% MeOH in $CH_2Cl_2$) followed by recrystallization (hexanes/$CH_2Cl_2$) to provide a white solid.

Elemental Analysis:
    Calcd: C, 67.32; H, 5.93; N, 7.85;
    Found: C, 67.22; H, 5.90; N, 7.80.
MS(FD): 356,322 (356.86).
$^1$H NMR ($d_6$-DMSO): δ1.92–2.24 (m, 4H); 2.37 (m, 4H); 3.39 (d, J=5.9 Hz, 2H); 6.81 (t, J=6.6 Hz, 1H); 6.93 (t, J=7.0 Hz, 1H); 7.21 (t, J=7.7 Hz, 1H); 7.29 (t, J=7.4 Hz, 1H); 7.34–7.47 (m, 3H); 7.53 (d, J=8.1 Hz, 2H); 8.08 (m, 2H)
IR (KBr): 3331, 1709, 1648, 1569, 690; cm–1.

EXAMPLE 33

N-(2-Chlorophenyl)-N'-[1-(1"-phenyl-cyclohex-3'-ene)methyl]-urea

A cold (0° C.) mixture of the compound of Example 31C (0.3 g, 0.8 mmol) and $Et_3N$ (0.2 ml, 1.2 mmol) in 2.0 ml of $CH_2Cl_2$, under $N_2$, was treated with methanesulfonyl chloride (0.08 ml, 1.0 mmol). The reaction mixture was stirred overnight at room temperature and then diluted with 20 ml of $CH_2Cl_2$, washed sequentially with 0.2N HCl, $NaHCO_3$ and brine, dried over $Na_2SO_4$, filtered and then concentrated in vacuo to provide 0.33 g (96%) of the mesylate.

A solution of the mesylate (0.33 g) and 1,8-diazabicyclo-[5.4.0]-undec-7-ene (0.4 ml, 2.4 mmol) in 7 ml of toluene was refluxed overnight and then concentrated in vacuo, diluted with $Et_2O$ and washed consecutively with 0.2N HCl, $NaHCO_3$ and brine, dried over $Na_2SO_4$, filtered and then concentrated in vacuo. The crude material was purified using flash chromatography (eluent of 10% EtOAc in hexanes).
Yield: 0.03 g of a white solid (12%).

Elemental Analysis:
  Calcd: C, 70.48; H, 6.21; N, 8.22;
  Found: C, 68.70; H, 6.24; N, 7.79.
MS(FD): 340.2 (340.86).
$^1$H NMR (d$_6$-DMSO): δ1.64 (m, 1H); 1.95 (m, 3H); 2.28 (m, 1H); 2.41 (m, 1H); 3.37 (m, 2H); 5.58 (m, 1H); 5.73 (m, 1H); 6.71 (m, 1H); 6.91 (m, 1H); 7.22 (m, 2H); 7.30–7.44 (m, 5H); 8.09 (s, 1H) and 8.10 (dd, J=1.5,8.1 Hz, 1H).

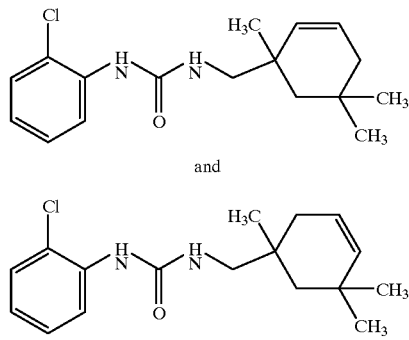

and

The compounds were prepared substantially in accordance with the procedure detailed in Example 33, using the compound of Example 3 (1.27 g, 3.9 mmol), Et$_3$N (0.8 ml, 5.9 mmol), methanesulfonyl chloride (0.3 ml, 4.3 mmol) and 3.0 ml of CH$_2$Cl$_2$ to provide the mesylate (1.56 g, 99%). Then, the mesylate (1.56 g) in 7 ml of toluene was reacted with 1,8-diazabicyclo-[5.4.0]-undec-7-ene (0.9 ml, 5.8 mmol). The crude material was purified using flash chromatography (eluent of 25% EtOAc in hexanes) to provide a mixture of the compounds.
Yield: 0.38 g of a white solid (32%).

EXAMPLE 35

N-(2-Chlorophenyl)-N'-[(1,3,3-trimethylcyclohexyl)methyl]-urea

The compound was prepared substantially in accordance with the procedure detailed in Example 27C, using a mixture of the compounds of Example 34 (0.23 g, 0.8 mmol), 50 ml of EtOAc, 35 ml of ammonia and platinum oxide (22 mg). The reaction mixture was filtered through celite and the filtrate was concentrated in vacuo. The crude material was purified using flash chromatography (eluent of 20% EtOAc in hexanes).
Yield: 0.18 g of a white solid (80%).
Elemental Analysis:
  Calcd: C, 66.11; H, 8.16; N, 9.07;
  Found: C, 66.73; H, 8.27; N, 8.73.
MS(FD): 308.4 (308.85).
$^1$H NMR (d$_6$-DMSO): δ0.92 (s, 6H); 0.95 (s, 3H); 1.07–1.35 (m, 6H); 1.49 (m, 2H); 2.89 (dd, J=6.1, 13.2 Hz, 1H); 3.02 (dd, J=6.1,13.2 Hz, 1H); 6.93 (m, 2H); 7.22 (m, 1H); 7.39 (dd, J=1.5,8.1 Hz, 1H); 8.09 (s, 1H); 8.18 (dd, J=1.5,8.1 Hz, 1H).
IR (KBr): 3339, 3300, 2903, 1644, 1586, 1437 and 740 cm$^{-1}$.

EXAMPLE 36

A. N-t-Butoxycarbonyl-2,2-diphenylethylamine

A solution of 2,2-diphenylethylamine (4.05 g, 20.5 mmol) in 75 ml of CH$_2$Cl$_2$, was treated with di-t-butyl dicarbonate (5.37 g, 24.6 mmol), under N$_2$. After 15 minutes, the reaction mixture was washed sequentially with NaHCO$_3$ and brine, dried over Na$_2$SO$_4$, filtered and then concentrated in vacuo. The crude material was purified by recrystallization (hexanes/CH$_2$Cl$_2$).
Yield: 4.41 g of a tan solid (73%).
$^1$H NMR (d$_6$-DMSO): δ1.28 (s, 9H), 3.52 (m, 2H), 4.15 (t, 1H), 6.80 (t, 1H) and 7.10–7.30 (m, 10H).

B. N-t-Butoxycarbonyl-N-methyl-2,2-diphenylethylamine

A solution of the compound of Example 36A (2.85 g. 9.6 mmol) in 30 ml of DMF was treated with sodium hydride (NaH) (60%, 0.38 g, 9.6 mmol), under N$_2$. After 30 minutes, iodomethane (5.0 ml, 80 mmol) was added and the mixture was stirred for another 30 minutes and then partitioned between Et$_2$O and H$_2$O. The resultant layers were separated and the organic layer was dried over Na$_2$SO$_4$, filtered and concentrated in vacuo.
Yield: 2.54 g (85%).

C. N-Methyl-2,2-diphenylethylamine

A solution of the compound of Example 36B (2.54 g, 8.2 mmol) and trifluoroacetic acid (3.1 ml, 40.8 mmol) in 10 ml of CH$_2$Cl$_2$, under N$_2$, was stirred for 6 hours and then concentrated in vacuo to provide an oil. This oil was diluted with CH$_2$Cl$_2$, washed sequentially with NaHCO$_3$ and brine, dried over Na$_2$SO$_4$, filtered and then concentrated in vacuo.
Yield: 1.73 g of an oil.
$^1$H NMR (d$_6$-DMSO): δ2.24 (s, 3H), 3.07 (d, 2H), 4.08 (t, 1H), 7.10–7.35 (m, 10H).

D. N-(2-Chlorophenyl)-N'-(2,2-diphenylethyl)-N'-methyl-urea

The compound was prepared substantially in accordance with the procedure detailed in Example 1, using the compound of Example 36C (0.50 g, 2.4 mmol) and 2-chlorophenyl isocyanate (0.3 ml, 2.6 mmol) in 2 ml of DMF. The crude material was purified by recrystallization (hexanes/Et$_2$O).
Yield: 0.63 g of a white solid (73%).
Elemental Analysis:
  Calcd: C, 72.42; H, 5.80; N, 7.68;
  Found: C, 72.53; H, 5.98; N, 7.65.
MS(FD): 364.1 (364.88).
$^1$H NMR (d$_6$-DMSO): δ2.73 (s, 3H); 4.02 (d, J=8.1 Hz, 2H); 4.44 (t, J=8.1 Hz, 1H); 7.12 (m, 1H); 7.15–7.50 (m, 13H) and 7.80 (s, 1H).
IR (KBr): 3443, 3023, 1672, 1594, 1523, 1301 and 763 cm$^{-1}$.

EXAMPLE 37

A. 2-Ethylphenyl isocyanate

The compound was prepared substantially in accordance with the procedure detailed in Example 27A, using 2-ethylaniline (1.5 ml, 12.2 mmol), Et$_3$N (4.3 ml, 30.4 mmol) and triphosgene (1.2 g, 4.0 mmol) in 45 ml of CH$_2$Cl$_2$.
Yield: 1.03 of an orange oil (57%).

B. N-(2-Ethylphenyl)-N'-(2,2-diphenylethyl)-N'-methyl-urea

The compound was prepared substantially in accordance with the procedure detailed in Example 36, using the compound of Example 36C (0.4 g, 1.9 mmol) and 2-ethylphenyl isocyanate (0.3 g, 2.0 mmol) in 4 ml of DMF. The crude material was purified using flash chromatography (eluent of 25% EtOAc in hexanes).
Yield: 0.56 g of a white solid (82%).
Elemental Analysis:
    Calcd: C, 80.41; H, 7.31; N, 7.81;
    Found: C, 80.35; H, 7.51; N, 7.91.
MS(FD): 358.1 (358.49).
$^1$H NMR (d$_6$-DMSO): δ1.07 (t, J=7.7 Hz, 3H); 2.44 (q, J=7.7,15.1 Hz, 2H); 2.74 (s, 3H); 3.98 (d, J=8.1 Hz, 2H); 4.42 (t, J=8.1 Hz, 1H); 7.00–7.45 (m, 14H); 7.66 (s, 1H).
IR (KBr): 3301, 1634, 1524, 1493 and 701 cm$^{-1}$.

EXAMPLE 38

N-(2-Ethylphenyl)-N'-(2,2-diphenylethyl)-urea

The compound was prepared substantially in accordance with the procedure detailed in Example 1, using the compound of Example 37A (0.3 g, 2.0 mmol) and 2,2-diphenylethylamine (0.4 ml, 1.9 mmol) in 4 ml of DMF. The crude material was purified using flash chromatography (eluent of 25% EtOAc in hexanes).
Yield: 0.41 g of a white solid (63%).
Elemental Analysis:
    Calcd: C, 80.20; H, 7.02; N, 8.13;
    Found: C, 79.90; H, 7.20; N, 8.19.
MS(FD): 344.0 (344.46).
$^1$H NMR (d$_6$-DMSO): δ1.06 (t, J=7.7 Hz, 3H); 2.44 (q, J=7.4,14.7 Hz, 2H); 3.76 (dd, J=5.9,7.7 Hz, 2H); 4.19 (t, J=8.1 Hz, 1H); 6.50 (t, J=5.5 Hz, 1H); 6.91 (m, 1H); 7.08 (m, 2H); 7.15–7.40 (m, 10H); 7.62 (s, 1H); 7.73 (d, J=8.5 Hz, 1H).
IR (KBr): 3352, 3304, 1640, 1563, 1452, 1241 and 745 cm$^{-1}$.

EXAMPLE 39

A. Trans-β-methylcinnamic acid

A mixture of ethyl trans-β-cinnamate (2.98 g, 15.7 mmol), 50 ml of 5N NaOH and 50 ml of EtOH was refluxed for 20 minutes. The resultant mixture was concentrated in vacuo, washed with EtOAc, cooled to 0° C. and acidified to pH 5 with 5N HCl and then concentrated in vacuo to provide a tan precipitate which was isolated by filtration, washed with H$_2$O and dried in vacuo. The resultant solid recrystallized from EtOH/H$_2$O.
Yield: 1.11 g of a white solid (32%).
$^1$H NMR (d$_6$-DMSO): δ2.62 (s, 3H), 6.18 (s, 1H), 7.36–7.43 (m, 3H), 7.47–7.54 (m, 2H).
IR (KBr): 3400–3700, 1676, 1616 and 1222 cm$^{-1}$.
MS(FD) 162.
Elemental Analysis:
    Calcd: C, 74.07; H, 6.11;
    Found: C, 74.06; H, 6.22.

B. 5,5-Dimethyl-3-phenyl-2-cyclohexenone

A cold (−78° C.) dilute solution of lithium diisopropylamide (2.0M in heptane/THF/ethylbenzene, 9.8 ml, 19.6 mmol) in 10 ml of THF, under N$_2$, was treated dropwise with a solution of the compound of Example 39A (0.95 g, 5.9 mmol) in 10 ml of THF. The resultant mixture was warmed to 0° C., stirred for 20 minutes and then cooled to −78° C. followed by the dropwise addition of a solution of 3,3-dimethylacrylic acid (0.59 g, 5.9 mmol) in 10 ml of THF. The reaction mixture was stirred at room temperature overnight, poured into 20 ml of H$_2$O and then concentrated and washed three times with Et$_2$O. The aqueous layer was acidified with 8.0 ml of 5N HCl, then heated to 30–35° C. and stirred for 1 hour. After cooling to room temperature, the desired compound was extracted with EtOAc (3×20 ml). The combined EtOAc extracts were washed sequentially with NaHCO$_3$ and brine, dried over Na$_2$SO$_4$, filtered and concentrated in vacuo. The crude material was purified using flash silica gel chromatography (eluent of 15% EtOAc in hexanes).
Yield: 0.82 g of a yellow oil (69% with minor impurities).
$^1$H NMR (CDCl$_3$): δ1.14 (s, 6H), 2.36 (s, 2H), 2.66 (d, J=1.5 Hz, 2H), 6.43 (t, J=1.5 Hz, 1H), 7.39–7.46 (m, 3H), 7.50–7.58 (m, 2H).
IR (CHCl$_3$): 2962 and 1656 cm$^{-1}$.
Elemental Analysis:
    Calcd: C, 83.87; H, 7.97
    Found: C, 83.96; H, 8.05.

C. 3-Cyano-5,5-dimethyl-3-phenyl cyclohexanone

A cold (15° C.) mixture of the compound of Example 39B (0.71 g, 3.6 mmol) in 60 ml of THF, under N$_2$, was treated with diethylaluminum cyanide (1.0M in toluene, 10.6 ml, 10.6 mmol). After stirring at 15° C. for 2 hours and then at room temperature overnight, the reaction mixture was poured into 70 ml of ice cold 2N NaOH. The resultant layers were separated and the organic layer was concentrated in vacuo. The crude material was purified using flash chromatography (eluent of 15% EtOAc in hexanes).
Yield: 0.58 g of a bright yellow liquid (71% with minor impurities).
$^1$H NMR (CDCl$_3$): δ1.04 (s, 3H), 1.32 (s, 3H), 2.10–2.47 (m, 4H), 2.92 (s, 2H), 7.31–7.57 (m, 5H).
IR (CHCl$_3$): 3021, 2239 and 1720 cm$^{-1}$.
MS(FD): 227.
Elemental Analysis:
    Calcd: C, 80.46; H, 7.75; N, 5.28;
    Found: C, 79.26; H, 7.54; N, 6.16.

D. 3-Cyano-5,5-dimethyl-3-phenylcyclohexanol (cis and trans)

A cold (0° C.) solution of the compound of Example 39C (0.58 g, 2.6 mmol) in MeOH (10 ml), under N$_2$, was treated with sodium borohydride (0.11 g, 3.0 mmol). After stirring at room temperature for 30 minutes, the reaction was quenched with ice, concentrated in vacuo and then partitioned between CH$_2$Cl$_2$ and H$_2$O. The resultant layers were separated and the organic layer was dried over Na$_2$SO$_4$, filtered and then concentrated in vacuo. The crude material was purified using flash chromatography (eluent of 20% ethyl acetate in hexanes).
Yield: 0.36 g of a clear oil (62%).
IR (CHCl$_3$): 2957, 2233 and 1009 cm$^{-1}$.
MS(FD): 229.
Elemental Analysis:
    Calcd: C, 78.56; H, 8.35; N, 6.11;
    Found: C, 78.25; H, 8.35; N, 5.85.

E. 3-Aminomethyl-5,5-dimethyl-3-phenylcyclohexanol (cis and trans)

The compound was prepared substantially in accordance with the procedure detailed in Example 12B, using the compound of Example 39D.

EXAMPLE 40

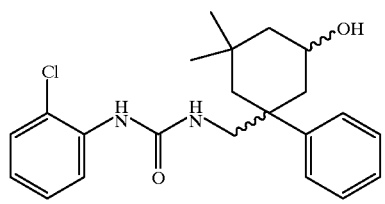

A solution of the compound of Example 39E (0.3 g, 1.3 mmol) and 2-chlorophenyl isocyanate (0.15 ml, 1.2 mmol) were reacted at room temperature for 1 hour. The mixture was then washed sequentially with $Na_2CO_3$ and brine, dried over $Na_2SO_4$, filtered and concentrated. The crude material was purified by recrystallization (hexanes/$Et_2O$).
Yield: 0.09 g of a white solid.
MS(FD): 386.3.
Elemental Analysis:
  Calcd: C, 68.29; H, 7.03; N, 7.24;
  Found: C, 68.50; H, 7.05; N, 7.16.

EXAMPLE 41

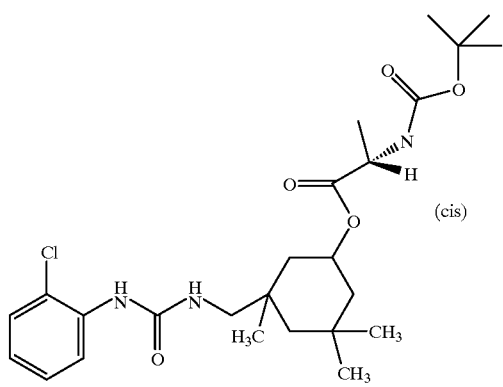

A mixture of the compound of Example 3A (0.50 g, 1.5 mmol), 1,3-dicyclohexyl carbodiimide (DCC) (0.37 g, 1.8 mmol), N-t-butoxycarbonyl-L-alanine (0.34 g, 1.8 mmol) and 4-dimethylaminopyridine (0.024 g, 0.2 mmol) in 125 ml of $Et_2O$ was stirred at room temperature overnight. The mixture was then filtered, and the filtrate was washed sequentially with water and 5% acetic acid, dried over $NaSO_4$, filtered and then concentrated in vacuo. The crude material was purified using flash chromatography (eluent of 25% EtOAc in hexanes).
MS(FD): 495.

EXAMPLE 42

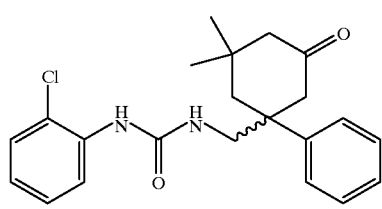

The compound of Example 40 was oxidized substantially in accordance with the procedure detailed in Example 32.

EXAMPLE 43

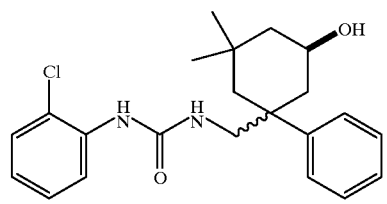

and

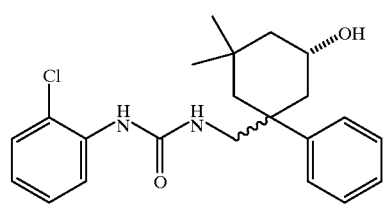

The compound of Example 42 was reduced substantially in accordance with the procedure detailed in Example 39D to provide a mixture of diastereomers. These diastereomers were separated by recrystallization from hexane/$Et_2O$.

As noted above, the compounds of the present invention are useful for inhibiting an envelope virus that undergoes hemagglutinin-mediated fusion with the host cell. An embodiment of the present invention is a method of treating or preventing a viral infection where the virus is an envelope virus that undergoes hemagglutinin-mediated fusion with the host cell which comprises administering to a virus-infected cell, a cell susceptible to infection or a mammal in need thereof an effective amount of a compound of formula I or a pharmaceutically acceptable salt thereof. Another embodiment of the present invention is a method of treating or preventing the symptoms associated with a viral infection comprising administering to a mammal in need thereof an effective amount of a compound of formula I or a pharmaceutically acceptable salt thereof. A further embodiment of the present invention is a method of inhibiting viral replication comprising administering to a virus-infected cell, a cell susceptible to infection or a mammal in need thereof, an effective amount of a compound of formula I or a pharmaceutically acceptable salt thereof.

The term "effective amount" as used herein, means an amount of a compound of the present invention which is capable of inhibiting the hemagglutinin mediated fusion of the virus with the host cell. The viral inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Active ingredient | 250 |
| Cellulose, Microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Active ingredient | 0.25 |
| Methanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 mL per minute.

The following experiment(s) was/were carried out to demonstrate the ability of the compounds of the present invention to inhibit influenza.

Plaque Reduction Assay

Susceptible MDCK cells were grown in 6 well tissue culture treated cluster plates at $1\times10^6$ cells/well in Minimum 199 with 1 percent fetal bovine serum, penicillin (100 units/ml) and streptomycin (100 µg/ml). After overnight incubation at 37° C., the growth medium was removed and 0.2 ml/well of an appropriate dilution of virus was added. After adsorption for 1–2 hour at room temperature, the infected cell sheet was overlaid with equal parts of 1.5% sterile agarose solution and a twofold concentration of medium 199 (with 2% fetal bovine serum, 100 units/ml of penicillin and 100 µg/ml streptomycin) containing varying concentrations of compounds.

The compounds were dissolved in DMSO at a concentration of 20 mg/ml and an aliquot was diluted to the desired concentration in DMSO and then added to the agar medium mixture. The plates were incubated in a $CO_2$ incubator at 37° C. until the DMSO control wells contained plaques of optimal size. Then, a solution containing 10 percent formalin and 2 percent sodium acetate was added to each well to inactivate the virus and fix the cell sheet to the plastic surface. The fixed cell sheets were stained with 0.5 percent crystal violet and the plaques were counted. Results from duplicate wells at each concentration were averaged and compared with DMSO control wells. The inhibition of plaque formation by 50 or 90 percent ($IC_{50}$ or $IC_{90}$) was calculated from the linear region of the inhibition concentration curve using the method of Reed and Muench, Am. J. Hyg., vol. 27, pages 493–497 (1958).

Using this plaque reduction assay, the $IC_{50}$ of the compounds of formula I with influenza A/Kawasaki was determined to be in the range of 0.02 µg/ml to 18.98 mg/ml.

What is claimed is:

1. A method of treating or preventing a viral infection where the virus is an envelope virus that undergoes hemagglutinin-mediated fusion with a host cell which comprises administering to a virus-infected cell, a cell susceptible of infection or a mammal in need thereof an effective amount of a compound of formula I:

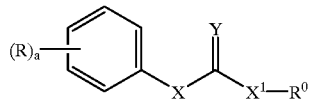

wherein:
a is 1, 2 or 3;
X is a bond, —NH—, —$CH_2$—, —O— or —S—;
Y is oxygen, sulfur or nitrogen;
R is halo or $C_1$–$C_4$ alkyl or $C_1$–$C_4$ alkoxy;
$X^1$ is —O—, —N($R^1$)— or —$CH_2$—;
$R^0$ is a group of the formula:

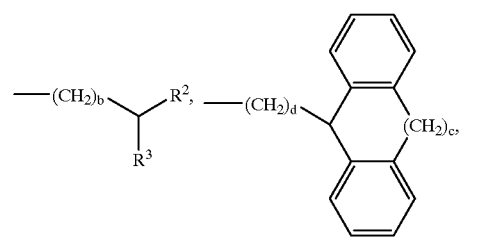

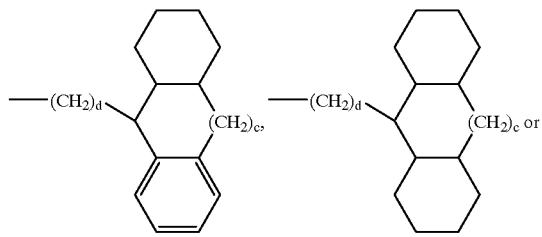

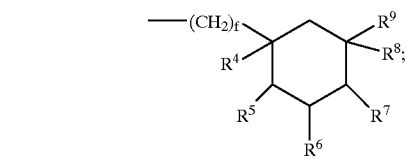

where:
$R^1$ is hydrogen, $C_1$–$C_4$ alkyl, benzyl or pyridyl ($C_1$–$C_4$ alkyl), thienyl ($C_1$–$C_4$ alkyl) or furyl ($C_1$–$C_4$ alkyl);

each b, d and f are independently 1, 2 or 3;

c is 0, 1 or 2;

$R^2$ and $R^3$ are independently hydrogen, phenyl, pyridyl, thiazolyl, quinolyl, tetrahydroquinolyl, cyclohexyl, cyclohexenyl or phenyl or pyridyl substituted with halo, $C_1$–$C_4$ alkyl or $C_1$–$C_4$ alkoxy;

$R^4$ is hydrogen, $C_1$–$C_4$ alkyl or phenyl;

$R^5$ is hydrogen or $R^5$ and $R^6$ combine to form a bond;

$R^6$ and $R^7$ are independently hydroxy, —OC(O)CH$_3$, =O, —OC(O)NHR$^{6a}$, —O—(R$^{6b}$)$_x$— or $R^6$ and $R^7$ combine to form a bond;

$R^{6a}$ is hydrogen, $C_1$–$C_4$ alkyl, phenyl or benzyl;

$R^{6b}$ is an amino acid;

x is 1, 2 or 3;

$R^8$ and $R^9$ are independently hydrogen or $C_1$–$C_4$ alkyl;

with the proviso that when $R^5$ and $R^6$ combine to form a bond, $R^7$ must be hydrogen, and when $R^6$ and $R^7$ combine to form a bond, $R^5$ must be hydrogen;

or a pharmaceutically acceptable salt thereof.

2. A method of inhibiting an envelope virus that undergoes hemagglutinin-mediated fusion with a host cell which comprises administering to a virus-infected cell, a cell susceptible of infection or a mammal in need thereof, an effective amount of a compound of formula I or a pharmaceutically acceptable salt thereof.

3. A method as claimed in claim 1 or 2 where the virus is influenza, bovine diarrheal, hepatitis C or tick borne encephalitis virus.

4. A method as claimed in any of claims 1 to 3 where the compound is one wherein:

a is 1 or 2;

Y is oxygen or sulfur;

R is halo, methyl or ethyl;

$R^1$ is hydrogen or methyl;

b, d and f are each 1;

c is 0 or 2;

$R^2$ and $R^3$ are independently phenyl, pyridyl, quinolyl, tetrahydroquinolyl or cyclohexyl;

or a pharmaceutically acceptable salt thereof.

5. A method as claimed in any of claims 1 to 4 where the compound is one wherein:

X is —NH— or —CH$_2$—;

$R^0$ is a group of the formula:

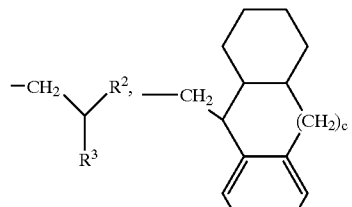

or

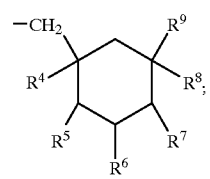

$R^4$ is hydrogen, methyl or phenyl;

$R^5$ is hydrogen or $R^5$ and $R^6$ combine to form a bond;

$R^6$ and $R^7$ are independently hydroxy, —OC(O)CH$_3$, =O, or $R^6$ and $R^7$ combine to form a bond;

$R^8$ and $R^9$ are independently hydrogen or methyl;

with the proviso that when $R^5$ and $R^6$ combine to form a bond, $R^7$ must be hydrogen, and when $R^6$ and $R^7$ combine to form a bond, $R^5$ must be hydrogen;

or a pharmaceutically acceptable salt thereof.

* * * * *